(12) United States Patent
Sasaki et al.

(10) Patent No.: US 7,638,035 B2
(45) Date of Patent: Dec. 29, 2009

(54) ELECTRODE PLATE FOR ELECTROCHEMICAL MEASUREMENTS

(75) Inventors: Hidehiro Sasaki, Osaka (JP); Akio Oki, Kyoto (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/363,118

(22) Filed: Jan. 30, 2009

(65) Prior Publication Data

US 2009/0145780 A1 Jun. 11, 2009

Related U.S. Application Data

(63) Continuation of application No. PCT/JP2008/001893, filed on Jul. 15, 2008.

(30) Foreign Application Priority Data

Jul. 20, 2007 (JP) ............................. 2007-189006

(51) Int. Cl.
*G01N 27/30* (2006.01)
(52) U.S. Cl. ................... 205/775; 205/777.5; 204/400; 204/403.01; 204/411
(58) Field of Classification Search ................ 204/400, 204/409, 411, 403.01; 205/775, 777.5
See application file for complete search history.

(56) References Cited

U.S. PATENT DOCUMENTS

| | | | | |
|---|---|---|---|---|
| 6,471,838 | B1 * | 10/2002 | Igel et al. ................ | 204/403.01 |
| 7,250,115 | B2 * | 7/2007 | Barth ...................... | 216/56 |
| 7,455,756 | B2 * | 11/2008 | Choi et al. .............. | 204/403.01 |
| 2004/0063152 | A1 | 4/2004 | Gumbrecht et al. | |

FOREIGN PATENT DOCUMENTS

| | | |
|---|---|---|
| JP | 02-268265 | 11/1990 |
| JP | 04-136748 | 5/1992 |
| JP | 05-002007 | 1/1993 |

(Continued)

OTHER PUBLICATIONS

Horiuchi, T., et al., "Limiting Current Enhancement by Self-Induced Redox Cycling on a Micro-Macro Twin Electrode", J. Electrochem. Soc., Dec. 1991, pp. 3549-3553, vol. 138 No. 12, The Electrochemical Society, Inc.

(Continued)

*Primary Examiner*—Kaj K Olsen
(74) *Attorney, Agent, or Firm*—McDermott Will & Emery LLP

(57) ABSTRACT

An object of the invention is to provide an electrode plate for electrochemical measurements for detecting with high sensitivity and determining a substance included in a living body. The electrode plate of the present invention has on both faces of body of the substrate, oxidation electrode and reduction electrode opened respectively at upper layer opening and lower layer opening having the same area; and further has a plurality of through-holes that penetrate through from the face of the oxidation electrode to the face of the reduction electrode, in which electrode pairs are formed which exhibit a redox cycle effect between the oxidation electrode and the reduction electrode by applying the potential which can proceed an oxidative reaction of a reductant on the oxidation electrode, and the potential which can proceed a reductive reaction of an oxidant on the reduction electrode.

18 Claims, 15 Drawing Sheets

FOREIGN PATENT DOCUMENTS

| | | |
|---|---|---|
| JP | 05-223772 | 8/1993 |
| JP | 06-027081 | 2/1994 |
| JP | 2556993 | 9/1996 |
| JP | 2564030 | 9/1996 |
| JP | 09-101283 | 4/1997 |
| JP | 3289059 | 3/2002 |
| JP | 2004-514890 | 5/2004 |
| JP | 2004-361189 | 12/2004 |
| JP | 2006-78404 | 3/2006 |
| JP | 2006-322813 | 11/2006 |
| JP | 2007-010429 | 1/2007 |
| WO | WO 02/42759 A1 | 5/2002 |

OTHER PUBLICATIONS

Aoki, K., et al., "Electrochemical Measurement Method Using Microelectrode", Feb. 10, 1998, pp. 48-49 and 70-71, The Institute of Electronics, Information and Communication Engineers.

* cited by examiner

ELECTRODE PLATE FOR ELECTROCHEMICAL MEASUREMENTS

This Application is a continuation of International Application No. PCT/JP2008/001893, whose international filing date is Jul. 15, 2008 which in turn claims the benefit of Japanese Patent Application No. 2007-189006, filed on Jul. 20, 2007, the disclosures of which Applications are incorporated by reference herein.

BACKGROUND OF THE INVENTION

1. Field of the Invention

The present invention relates to an electrode plate for electrochemical measurements for detecting with high sensitivity and determining quantitatively a substance included in a living body in a slight amount.

2. Related Art

In recent years, electrode plates for electrochemical measurements for quantitatively determining the concentration of a saccharide such as sucrose, glucose or the like included in blood in a living body by a combination of a specific catalytic action of an enzyme and an electronic mediator having an electrode reaction activity.

According to such an electrode plate for electrochemical measurements, the reaction of a saccharide with an enzyme is utilized to quantitatively determine the concentration of the saccharide electrochemically. First, after a sample solution is prepared by mixing a blood sample with the enzyme and the electronic mediator, the enzymatic reaction is allowed between the saccharide and the enzyme. Thereafter, the electronic mediator coexisting therewith is electrochemically measured, whereby the saccharide included in the sample solution is quantitatively determined indirectly via the electronic mediator.

In this method, the enzymatic reaction is highly specific for the saccharide, accompanied by less influences from the temperature during operation, and the mechanism of the quantitative analysis unit is simple; therefore, ordinary persons can quantitatively determine the concentration of the saccharide in their own blood easily at home and the like by using this method.

The electrode plate for electrochemical measurements is suited for analyses of solution samples of a slight amount included in living bodies. Thus, applications of the electrode plate for electrochemical measurements have been attempted to sensors and the like through combining with a variety of organic materials or inorganic materials. The electrode response speed of the electrode plate for electrochemical measurements is accelerated as the area of a microelectrode carried by the electrode plate for electrochemical measurements is reduced. Therefore, various electrode shapes, and miniaturization of electrodes have been investigated.

However, as the area of the electrode is reduced, the resulting electric current value is lowered. For example, when the area of the electrode is miniaturized to approximately several hundred $\mu m^2$, detectable electric current value may be lowered to several ten to several nA order. Thus, increase in noise response, and deterioration of the sensitivity may be caused in measurement. Accordingly, in order to avoid these defects, electrode plates for electrochemical measurements in which a plurality of microelectrodes are integrated were studied as in Japanese Patent No. 2556993 (column 6, FIG. 1, Patent Document 1), Japanese Patent No. 2564030 (column 7, FIG. 2, Patent Document 2), Japanese Unexamined Patent Publication No. 2006-78404 (column 25, FIG. 1, Patent Document 3) and Japanese Patent No. 3289059 (page 16, FIG. 5, Patent Document 4).

In Patent Documents 1 to 4, methods of producing a large quantity of microelectrodes on a substrate while keeping a constant distance between adjacent microelectrodes with favorable reproducibility are proposed.

FIG. 1A and FIG. 1B show a construction of a conventional electrode plate for electrochemical measurements disclosed in Patent Document 1.

This electrode plate for electrochemical measurements 10 is constructed by laminating insulative substrate 1/bottom electrode 2 that functions as an oxidation electrode/insulating layer 3/surface electrode 4 that functions as a reduction electrode. A large number of cylindrical micropores 5 are formed on the surface of the surface electrode 4, and the surface of the bottom electrode 2 is exposed to the micropore 5.

The insulative substrate 1 is constituted with, for example, a silicon substrate with an oxide film, generally referred to, in which oxide film 1b is adhered on the main surface of silicon substrate 1a. The bottom electrode 2 is an oxidation electrode formed with a metal, a semimetal, a carbonic material, or a semiconductor on the surface of the oxide film 1b of the substrate 1 (i.e., insulator surface). The surface electrode 4 is a reduction electrode formed with a metal, a semimetal, or a semiconductor on the insulating layer 3, similarly to the bottom electrode 2. A working electrode pair is formed with the bottom electrode 2 and the surface electrode 4. In other words, both the bottom electrode 2 and the surface electrode 4 function as working electrodes, and more specifically, the bottom electrode 2 functions as an oxidation electrode, while the surface electrode 4 functions as a reduction electrode, as described above. In FIG. 1A and FIG. 1B, the reference numeric character 7 represents an opening for drawing the electrode, opened so as to connect an outer lead to one end of the bottom electrode 2. Herein, the micropore represents a hole that completely penetrates through the insulating layer 3 and the surface electrode 4, and then reaches to the surface of the bottom electrode 2.

In an apparatus for electrochemical measurements in which the electrode plate for electrochemical measurements as described above is used, a potential is applied between the bottom electrode 2 and the surface electrode 4 for achieving an electric current response. When the apparatus for electrochemical measurements is constructed with three electrodes, i.e., bottom electrode 2, surface electrode 4, and a counter electrode (not shown in the Figure), a potential is applied between the bottom electrode 2 and the counter electrode, and between the surface electrode 4 and the counter electrode, provided that the potential shown by the counter electrode in the sample solution is zero. In addition, when the apparatus for electrochemical measurements is constructed with four electrodes, i.e., bottom electrode 2, surface electrode 4, a reference electrode (not shown in the Figure), and an auxiliary electrode (not shown in the Figure), a potential is applied between the bottom electrode 2 and the reference electrode, and between the surface electrode 4 and the reference electrode, provided that the potential shown by the reference electrode in the sample solution is zero.

In Patent Document 4 and J. Electrochem. Soc., Vol. 138, No. 12, page 3551 (1991)(Nonpatent Document 1), an electrode plate for electrochemical measurements is proposed in which cylindrical micropores 5 are provided such that the intervals among them becomes greater than their diameter, and the results of electrochemical measurements using the same are reported. In these Documents, the surface electrode 4 that is a macroelectrode has an area greater than the bottom electrode 2 that is an assembly of microelectrodes. Upon measurement, potentials are applied, respectively, which can cause an oxidative reaction on the bottom electrode 2, and a reductive reaction on the surface electrode 4. It is reported that self-induced redox cycle is thus generated between the bottom electrode 2 and the surface electrode 4, whereby apparently high electric current response can be achieved.

In this manner, a target substance such as a saccharide is quantitatively determined via an electronic mediator that is present in a sample solution.

Alternatively, even though a potential that causes a reductive reaction is applied on the bottom electrode 2, while a potential that causes an oxidative reaction is applied on the top electrode 4, similar self-induced redox cycle is generated.

Hereinbelow, the self-induced redox cycle described in Patent Document 4, and Nonpatent Document 1 and Koichi Aoki et al., "Electrochemical Measurement Method Using Microelectrode" edited by The Institute of Electronics, Information and Communication Engineers, published on Feb. 10, 1998 pages 48-49 and 70-71 (Nonpatent Document 2) are explained with reference to FIG. 2.

The self-induced redox cycle in FIG. 2 proceeds on two working electrodes, i.e., microelectrode 21 and macroelectrode 22.

An oxidative reaction of reductant 23 is caused to produce oxidant 24 on the surface of the microelectrode 21, whereby an oxidation current flows to the microelectrode 21.

On the surface of a part 22a, which is close to the microelectrode 21, of the macroelectrode 22, the oxidant 24 is reduced to be converted into reductant 25, whereby a reductive electric current flows to the macroelectrode 22.

Furthermore, the reductant 25 is diffused to reach to the surface of the microelectrode 21, whereby an oxidative reaction is caused again from the reductant 23 to the oxidant 24, leading to an oxidation current to flow toward the microelectrode 21. As a consequence, the reductant 23 can be fed to the surface of the microelectrode 21 by reducing the oxidant 24 generated from the microelectrode 21 to give the reductant 25 on the surface of the macroelectrode 22a.

Accordingly, as a result of occurrence a so-called redox cycle reaction in which an oxidative reaction and a reductive reaction recur between the microelectrode 21 and the macroelectrode 22a, an electric current constantly flows to the microelectrode 21, and thus the target substance included in a sample solution in a slight amount can be detected and quantitatively determined.

Moreover, in order to improve the efficacy of the measurement with high sensitivity, electrode pairs consisting of an oxidation electrode and a reduction electrode by which a redox cycle proceeds are formed as many as possible through forming a larger number of the microelectrodes 21 on the substrate.

SUMMARY OF THE INVENTION

As shown in FIG. 1A and FIG. 1B, by providing surface electrode 4 that functions as a reduction electrode to have an area much greater than the area of bottom electrode 2 that functions as an oxidation electrode, a self-induced redox cycle is generated; however, this event may cause a problem as in the following.

Although reductant 25 formed on macroelectrode 22a is diffused, it reaches not only to the microelectrode 21 (corresponding to bottom electrode 2 in FIG. 1A and FIG. 1B), but in part, also onto a part 22b, which is far from the microelectrode 21, of the macroelectrode 22 (corresponding to surface electrode 4 in FIG. 2) as shown in FIG. 2, right side. Such a reductant 26 is converted into oxidant 27 by an oxidative reaction. In other words, an oxidative reaction is also caused on the macroelectrode 22 (see, also FIG. 4 in Japanese Unexamined Patent Application, First Publication No. Hei 3-246460).

Next, the oxidant 27 is diffused, and reaches onto a part 22a, which is close to the microelectrode 21, of the macroelectrode 22. The reductant 25 is yielded there by a reductive reaction. The reductant 25 is diffused, reaches onto the surface of the microelectrode 21, and oxidized again to be converted into oxidant 24 (alternatively, reaches again to a part 22b, which is far from the microelectrode 21, of the macroelectrode 22).

Accordingly, on the surface electrode 4 shown in FIG. 1, an oxidative reaction and a reductive reaction concomitantly occur. As a result, oxidation of the reductant, the detection of which should be effected on the bottom electrode 2, is also caused on the surface electrode 4 concomitantly.

Therefore, the reductant generated on the surface electrode 4 is not oxidized efficiently on the bottom electrode 2, thereby leading to problems in improvement of sensitivity.

Furthermore, according to a structure in which an electrode plate for electrochemical measurements is provided on only one face of the substrate as shown in FIG. 1, the area on which the electrode can be formed is restricted, thereby yet leading to problems in improvement of sensitivity.

In addition, since the surface electrode 4 operates as a macroelectrode, a great charge current is achieved in applying the potential. Thus, a problem of lengthening of the time required until the reaction reaches to a stationary state as compared with the bottom electrode 2 that is a microelectrode has also caused.

Means for Solving the Problems

The electrode plate for electrochemical measurements 10 according to the present invention which can solve the foregoing problems includes substrate 32 made of an insulator, upper layer 31 made of an insulator provided on the superior face of the substrate 32, and lower layer 33 made of an insulator provided on the inferior face of the substrate 32, wherein:

the substrate 32 includes a plurality of oxidation electrodes 32W sandwiched between the superior face of the substrate 32 and the upper layer 31, and a plurality of reduction electrodes 32$w$ sandwiched between the inferior face of the substrate 32 and the lower layer 33;

the upper layer 31 has a plurality of upper layer openings 31W;

each of the oxidation electrodes 32W is exposed from each of the upper layer openings 31W;

the lower layer 33 has a plurality of lower layer openings 33$w$;

each of the reduction electrodes 32$w$ is exposed from each of the lower layer openings 33$w$;

the substrate 32 is provided with a plurality of through-holes 32H that penetrate from the superior face of each of the oxidation electrodes 32W to the inferior face of each of the reduction electrodes 32$w$;

each of the upper layer openings 31W has the same area with the area of each of the lower layer openings 33$w$;

each of the upper layer openings 31W has an area of equal to or less than 10,000 $\mu m^2$, and each of the lower layer openings 33w has an area of equal to or less than 10,000 μm².

It is preferred that each of the upper layer openings has an area of equal to or greater than 225 μm², and each of the lower layer openings has an area of equal to or greater than 225 μm².

It is preferred that the through-hole has a cross sectional area of 1 μm² or greater and 2,500 μm² or less.

It is preferred that the lower layer has a thickness of 5 μm or greater and 100 μm or less.

This electrode plate for electrochemical measurements 10 is combined with reference electrode 42 and auxiliary electrode 43, or combined with a counter electrode to construct an apparatus for electrochemical measurements. This apparatus for electrochemical measurements is also included in principles of the present invention.

Furthermore, principles of the present invention also include a process for quantitatively determining a target substance included in a sample solution containing an electronic mediator with this apparatus for electrochemical measurements, as in the following.

A process for quantitatively determining a target substance included in a sample solution, with an apparatus for electrochemical measurements including a reference electrode, an auxiliary electrode and an electrode plate for electrochemical measurements, or a counter electrode and an electrode plate for electrochemical measurements, the process including the steps of:

preparing a sample solution containing an electronic mediator;

providing the electrode plate for electrochemical measurements;

bringing the reference electrode, the auxiliary electrode and the electrode plate for electrochemical measurements into contact with the sample solution, or bringing the counter electrode and the electrode plate for electrochemical measurements into contact with the sample solution;

measuring the electric current that flows each of the oxidation electrode plate and the reduction electrode, by sweeping a positive potential to the oxidation electrode plate and applying a negative potential to the reduction electrode plate, or by applying a positive potential to the oxidation electrode plate and sweeping a negative potential to the reduction electrode plate; and determining the amount of the target substance from the electric current derived in the step of measuring the electric current, wherein said electrode plate for electrochemical measurements including a substrate made of an insulator, an upper layer made of an insulator provided on the superior face of the substrate, and a lower layer made of an insulator provided on the inferior face of the substrate, wherein:

the substrate includes a plurality of oxidation electrodes sandwiched between the superior face of the substrate and the upper layer and a plurality of oxidation electrodes sandwiched between the inferior face of the substrate and the upper layer;

the upper layer has a plurality of upper layer openings;

each of the oxidation electrodes is exposed from each of the upper layer openings;

the lower layer has a plurality of lower layer openings;

each of the reduction electrodes is exposed from each of the lower layer openings;

the substrate is provided with a plurality of through-holes that penetrate from the superior face of each of the oxidation electrodes to the inferior face of each of the reduction electrodes;

each of the upper layer openings has the same area with the area of each of the lower layer openings;

each of the upper layer openings has an area of equal to or less than 10,000 μm², and each of the lower layer openings has an area of equal to or less than 10,000 μm².

It is preferred that the surface area of the auxiliary electrode be no less than 10 times greater than the assembly of the oxidation electrodes.

A mesh filter may be provided on the superior face of the upper layer.

It is preferred that the reference electrode be formed on the superior face of the upper layer, while the auxiliary electrode is formed on the inferior face of the lower layer.

According to the present invention, an electrode plate for electrochemical measurements for detecting with high sensitivity and determining quantitatively a substance included in a living body in a slight amount, an apparatus for electrochemical measurements having this electrode plate, and a process for quantitatively determining a target substance using this electrode plate are provided.

The aforementioned and other objects, features, and advantages of the present invention are clarified by the following detailed description of preferred embodiments with reference to accompanying drawings.

DETAILED DESCRIPTION OF THE INVENTION

Hereinafter, embodiments of the present invention will be explained with reference to the drawings.

Embodiment 1

Figure 3:
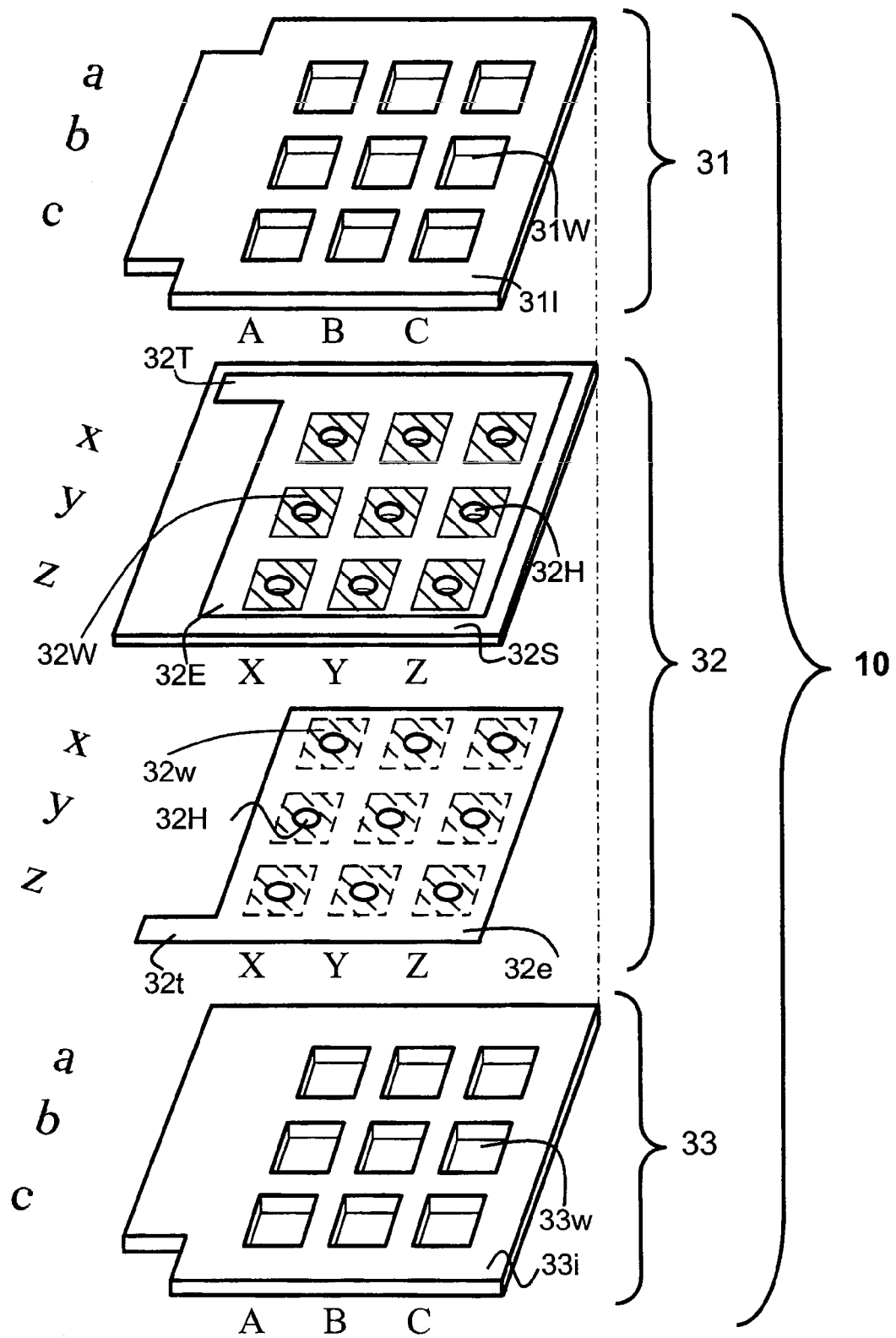
FIG. 3 shows an exploded perspective view illustrating an electrode plate for electrochemical measurements according to Embodiment 1 of the present invention.

FIG. 3 shows an exploded perspective view illustrating an electrode plate for electrochemical measurements according to this Embodiment 1.

As shown in FIG. 3, the electrode plate for electrochemical measurements 10 according to this Embodiment 1 is constructed by laminating lower layer 33, substrate 32, and upper layer 31 in this order from the downside. Both the lower layer 33 and the upper layer 31 are insulators.

The substrate 32 is constituted with a body of the substrate 32S made of an insulator. Oxidation electrode plate 32E is provided on the superior face of this body of the substrate 32S, while reduction electrode plate 32e is provided on the inferior face of this body of the substrate 32S. The oxidation electrode plate 32E is sandwiched between the body of the substrate 32S and the upper layer 31, as shown in FIG. 3. Similarly, the reduction electrode plate 32e is sandwiched between the body of the substrate 32S and the lower layer 33.

The upper layer 31 has a plurality of upper layer openings 31W. In FIG. 3, nine upper layer openings 31W are provided. A part of the oxidation electrode plate 32E is exposed from each upper layer opening 31W. Of the oxidation electrode plate 32E, a part exposed from each upper layer opening 31W, i.e., a hatched part on the oxidation electrode plate 32E in FIG. 3, is to be in contact with the sample solution, and thus functions as oxidation electrode 32W. In FIG. 3, nine oxidation electrodes 32W are provided. Of the oxidation electrode plate 32E, a part on which the upper layer 31 is formed, i.e., an unhatched and white part on the oxidation electrode plate 32E in FIG. 3 is not to be in contact with the sample solution. Thus, this part does not function as an oxidation electrode.

Similarly to the upper layer 31, the lower layer 33 also has a plurality of lower layer openings 33W. In FIG. 3, nine lower layer openings 33W are provided. A part of the reduction electrode plate 32e is exposed from each lower layer opening 33W. Of the reduction electrode plate 32e, a part exposed from each lower layer opening 33w, i.e., a hatched part on the reduction electrode plate 32e in FIG. 3, functions as reduction electrode 32w. In FIG. 3, nine reduction electrodes 32w are provided. Of the reduction electrode plate 32e, a part on which the lower layer 33 is formed, i.e., an unhatched and white part on the reduction electrode plate 32e in FIG. 3 is not to be in contact with the sample solution. Thus, this part does not function as a reduction electrode.

The potential can be applied independently to the oxidation electrode plate 32E and the reduction electrode plate 32e, respectively, and thus an electrochemical reaction of the target substance, more specifically, an oxidative reaction and a reductive reaction can be progressed on each electrode. The electronic signal generated by the electrochemical reaction on the oxidation electrode 32W transmits to the oxidation electrode plate 32E, and can be quantitatively determined by a measuring instrument such as a galvanometer via oxidation electrode lead 32T. In a similar manner, the electronic signal generated by the electrochemical reaction on the reduction electrode 32w transmits to the reduction electrode plate 32e, and can be quantitatively determined by a measuring instrument such as a galvanometer via reduction electrode lead 32t.

Each oxidation electrode 32W and each reduction electrode 32w are superposed with plane body of the substrate 32S interposed therebetween. In FIG. 3, oxidation electrodes 32W (vertical 3 columns×horizontal 3 rows), and reduction electrodes 32w (vertical 3 columns×horizontal 3 rows) are superposed with the body of the substrate 32S interposed therebetween.

In FIG. 3, for simplifying the explanation, the reduction electrode plate 32e is illustrated to separate from the body of the substrate 32S; however, the reduction electrode plate 32e is formed on the inferior face of the body of the substrate 32S, in practice.

The oxidation electrode plate 32E has oxidation electrode lead 32T at its one end. The electronic signal yielded by the oxidation electrode plate 32E can be taken out from the oxidation electrode lead 32T. Similarly, the reduction electrode plate 32e is also electrically conducted to the reduction electrode lead 32t, and the electronic signal yielded by the reduction electrode plate 32e can be taken out from the reduction electrode lead 32t.

The substrate 32 is provided with a plurality of through-holes 32H. Additionally, each through-hole 32H penetrates from the superior face of each oxidation electrode 32W to the inferior face of each reduction electrode 32w. In FIG. 3, nine sets including one oxidation electrode 32W, one through-hole 32H, and one reduction electrode 32w are illustrated.

When the through-hole 32H is not provided, quantitative determination of the target substance cannot be performed with high sensitivity, and a long period of time is required until reaching to a stationary state in the quantitative determination, as would be also understood from Comparative Example 1 described later.

The area of each upper layer opening 31W, i.e., the area of each oxidation electrode 32W is equal to or less than 10,000 $\mu m^2$. When this area is greater than 10,000 $\mu m^2$, an undesirable reaction as shown on the right side in FIG. 2 occurs, and consequently, problems in elevation of sensitivity may be caused. In other words, as also demonstrated in Comparative Example 2 described later, quantitative determination of the target substance cannot be performed with high sensitivity, and an additionally longer period of time is required until reaching to a stationary state in the quantitative determination. Similarly, the area of each lower layer opening 33w, i.e., the area of each reduction electrode 32w is also equal to or less than 10,000 $\mu m^2$.

The lower limit of the area of each upper layer opening 31W (i.e., the area of each oxidation electrode 32W) and the area of each lower layer opening 33w (i.e., the area of each reduction electrode 32w) is not particularly limited, but is preferably equal to or greater than 225 $\mu m^2$.

The area of each upper layer openings 31W and the area of each lower layer openings 33w are substantially the same. In other words, any of the area of the plurality of upper layer openings 31W is identical with one another. Similarly, any of the area of the plurality of lower layer openings 33W is identical with one another. In addition, the area of these upper layer openings 31W and the area of these lower layer openings 33W are identical. The cross sectional area of each through-hole 32H is preferably identical with one another.

Figure 1A:
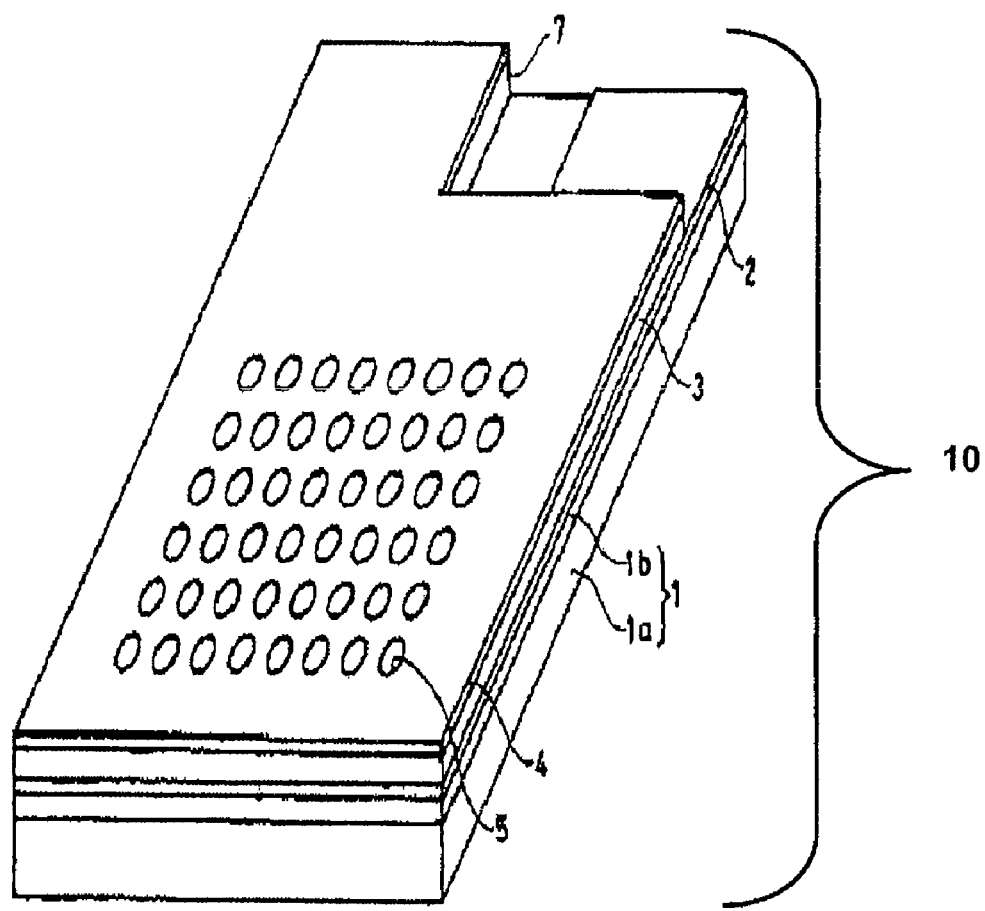
FIG. 1A shows an overall perspective view and FIG. 1B shows an enlarged perspective view illustrating a conventional electrode plate for electrochemical measurements disclosed in Patent Document 1.
Figure 1B:
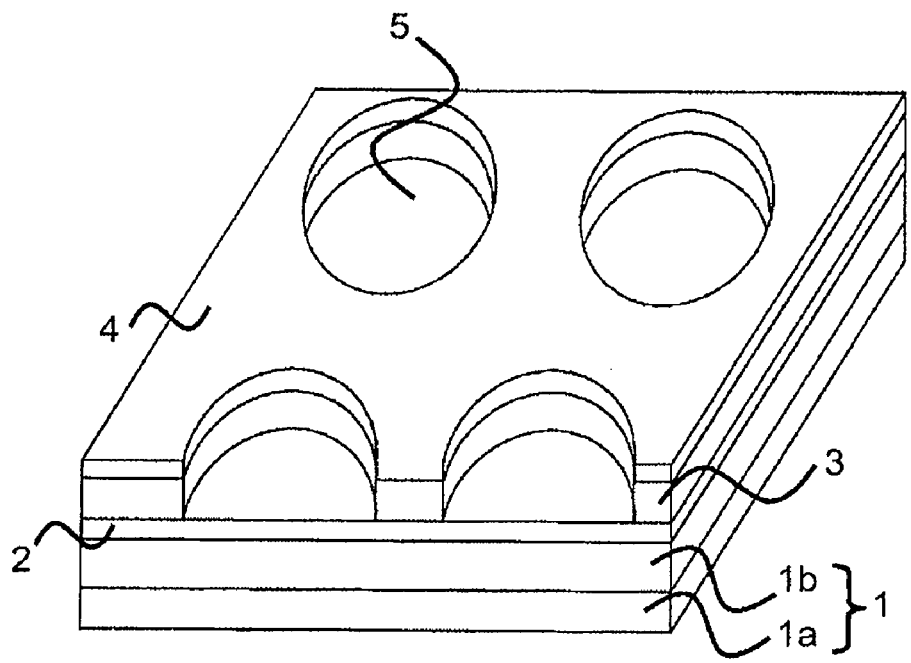
Figure 2:
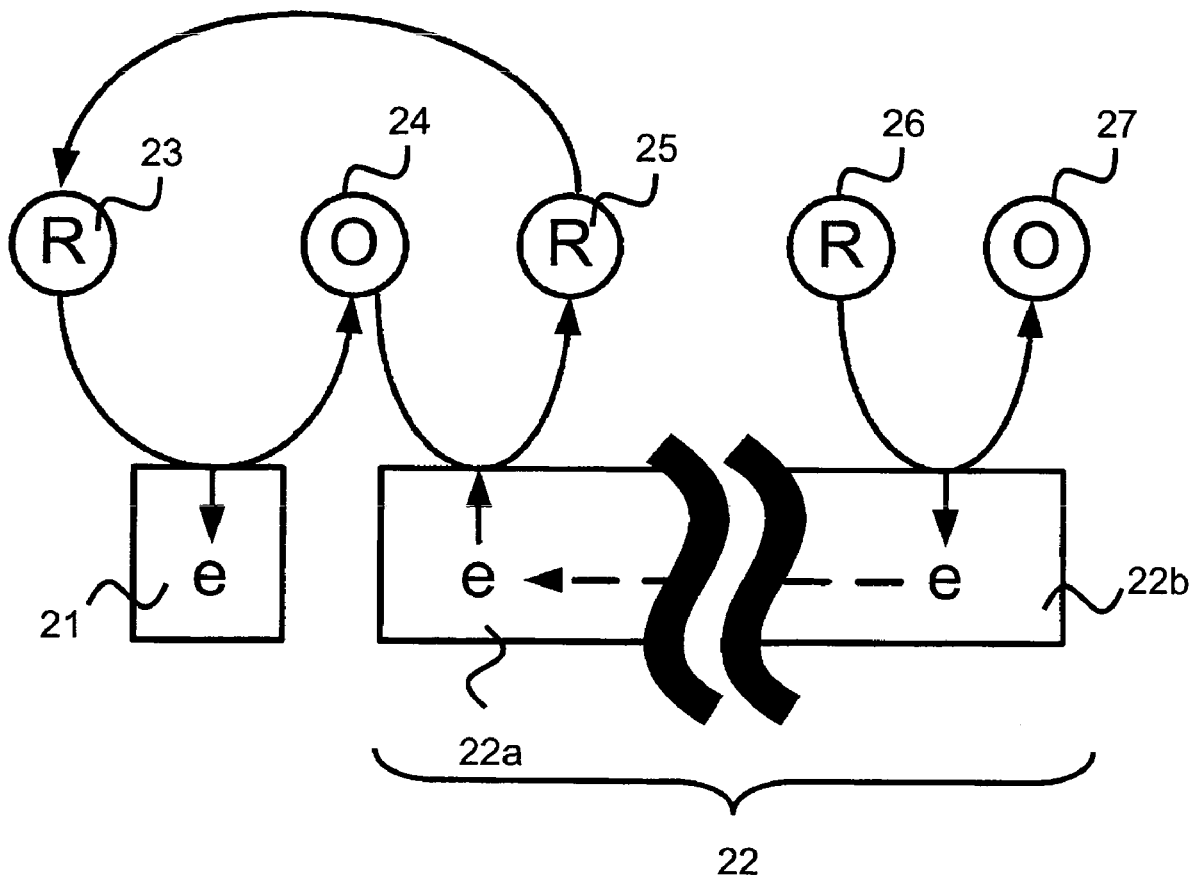
FIG. 2 shows a view illustrating a mechanism of a self-induced redox cycle disclosed in Patent Document 4, Non-patent Documents 1 and 2.

By setting the area of each upper layer opening 31W to be identical with the area of each lower layer opening 33w, the time period required for reaching to the stationary state can be shortened. Moreover, when the area of each upper layer opening 31W is different from the area of each lower layer opening 33w, the reaction as shown in FIG. 2 is caused, whereby elevation of sensitivity may be difficult.

As a matter of fact, the cross sectional area of the through-hole 32H is smaller than any of the area of the upper layer opening 31W and the area of the lower layer opening 33W. A set including one oxidation electrode 32W and one reduction electrode 32w may be provided with two or more through-holes 32H. However, to provide one through-hole 32H is enough in the case of such a set including one oxidation electrode 32W and one reduction electrode 32w, in terms of designing.

When the size of the cross sectional area of the through-hole 32H is as small as possible, formation of a large number of through-holes on the substrate 32 is enabled. This is preferred since electrode pairs including the oxidation electrode 32W and the reduction electrode 32w can be arranged in a larger number. However, to make the size of the cross sectional area of the through-hole 32H smaller tends to result in increase of the conductance required when the electronic mediator included in the sample solution passes the hole. To the contrary, the through-hole 32H having too large cross sectional area leads to the areas of each oxidation electrode 32W and each reduction electrode 32w, which must be equal to or less than 10,000 $\mu m^2$, to be diminished pointlessly. Therefore, preferable value of the cross sectional area of the through-hole 32H is 1 $\mu m^2$ or greater and 2,500 $\mu m^2$ or less.

The lower layer 33 has a thickness of 5 $\mu m$ or greater and 100 $\mu m$ or less. Since the distance between adjacent reduction electrodes 32w is approximately 7 $\mu m$ in general, two or more adjacent reduction electrodes 32w shall function as one continuous reduction electrode 32w in effect, when the lower layer 33 has a thickness of less than 5 $\mu m$. Thus, the undesirable reaction shown in right side of FIG. 2 is likely to be caused.

In other words, when the lower layer 33 has a thickness of less than 5 $\mu m$, the electronic mediator of the reduction pair generated on the reduction electrode 32w is more likely to become an oxidized mediator through oxidation on the adjacent reduction electrode 32w, than the reduced electronic mediator generated on the reduction electrode 32w to pass through the through-hole 32H and reach to the oxidation electrode 32W. To the contrary, the thickness of the lower layer 33 being greater than 100 $\mu m$ is not preferred since the amount of the sample solution to be required for accurate measurement is increased. This is applicable also to the upper layer 31.

Examples of the material of the body of the substrate 32S include, for example, silicon oxidized on both faces, glass, aluminum oxide, polyethylene terephthalate, polyethylene naphthalate, silicon resins, polyimide and derivatives thereof, epoxy resins, high molecular thermosetting materials, photo-sensitive resins, and the like.

In the electrode plate for electrochemical measurements of the present invention, the through-hole 32H serves as a path of the sample solution; therefore, the inner wall of the through-hole 32H is desirably hydrophilic when the sample solution is an aqueous solution. Thus, it is desired to select as the body of the substrate 32S, a substrate having a hydrophilic surface such as a silicon substrate or a glass substrate, or a substrate constructed with a hydrophilic polyester material such as a polyethylene terephthalate or polyethylene naphthalate substrate. When a hydrophobic substrate is used, it is desired to subject the inner wall of the through-hole 32H to a hydrophilizing treatment with ethanol, isopropyl alcohol or the like.

As the material of the oxidation electrode plate 32E (including oxidation electrode lead 32T), and the material of the reduction electrode plate 32e (including reduction electrode lead 32t), materials having an electrical conduction property can be exemplified. Specific examples of the material include metals such as gold, platinum, palladium, silver, chromium, titanium and nickel, semiconductors such as p-type silicon, n-type silicon, p-type germanium, n-type germanium, cadmium sulfide, titanium dioxide, zinc oxide, gallium phosphide, gallium arsenide, indium phosphide, molybdenum diarsenide, tungsten selenide, copper dioxide, tin oxide, indium oxide and indium tin oxide, and the like. Alternatively, an electrically conductive carbon such as Kechen black can be also used.

Among these, gold, platinum or palladium that is stable as an electrode material can be preferably used. In formation of these, methods in which a film forming process such as vapor deposition or sputtering is combined with an etching process may be employed. Screen printing in which a mask is used, a laser ablation method, or a spin coating method in which an electrically conductive ink is used, a direct drawing process by an ink jet printing method can be also employed.

As a process for forming the through-hole 32H, a dry etching method, a wet etching method, a lift off method, a process for forming a hole to a substrate which had been provided with electrodes by a processing method through irradiating a focused ion beam can be exemplified. Instead, it may be also formed by subjecting the substrate to out a hole formation processing according to the procedure described above, after patterning the through-hole 32H on the substrate using a metal mask. Alternatively, a method in which a substrate is formed on a mold having a relief pattern of the through-hole 32H, and the mold is removed after forming the electrode plate on the substrate, or a method in which the through-hole is formed on the substrate attached with the electrode plate using a heated mold, and thereafter the mold is removed may be also suggested.

As the process for forming the upper layer opening 31W and the lower layer opening 33w, a process of forming an opening to insulator 31I and insulator 33i by a dry etching method, a wet etching method, a lift off method, a process for forming a hole to a substrate which had been provided with electrodes by a processing method through irradiating a focused ion beam or the like can be exemplified. Alternatively, it may be also formed by a method using a photosensitive resin material such as a positive resist or a negative resist, in which a shielding mask such as a dry film resist is combined with an exposure process.

When the oxidation electrode plate 32E (including oxidation electrode lead 32T), the reduction electrode plate 32e (including reduction electrode lead 32t), the upper layer 31, and the lower layer 33 are formed by spin coating, it is desired to use a work table of the coater in which a porous material is employed. Since the electrode plate (oxidation electrode plate 32E and reduction electrode plate 32e), and the insulating layer (upper layer 31 and lower layer 33) are formed on both faces of the body of the substrate 32S, a vacuum adsorption method with a porous material is preferred for stably fixing the substrate, as compared with the case in which a coater head such as Teflon (registered trademark) provided with holes for adsorption at several sited of the material is used, due to increase of the area for adsorption and fixing.

Figure 4:
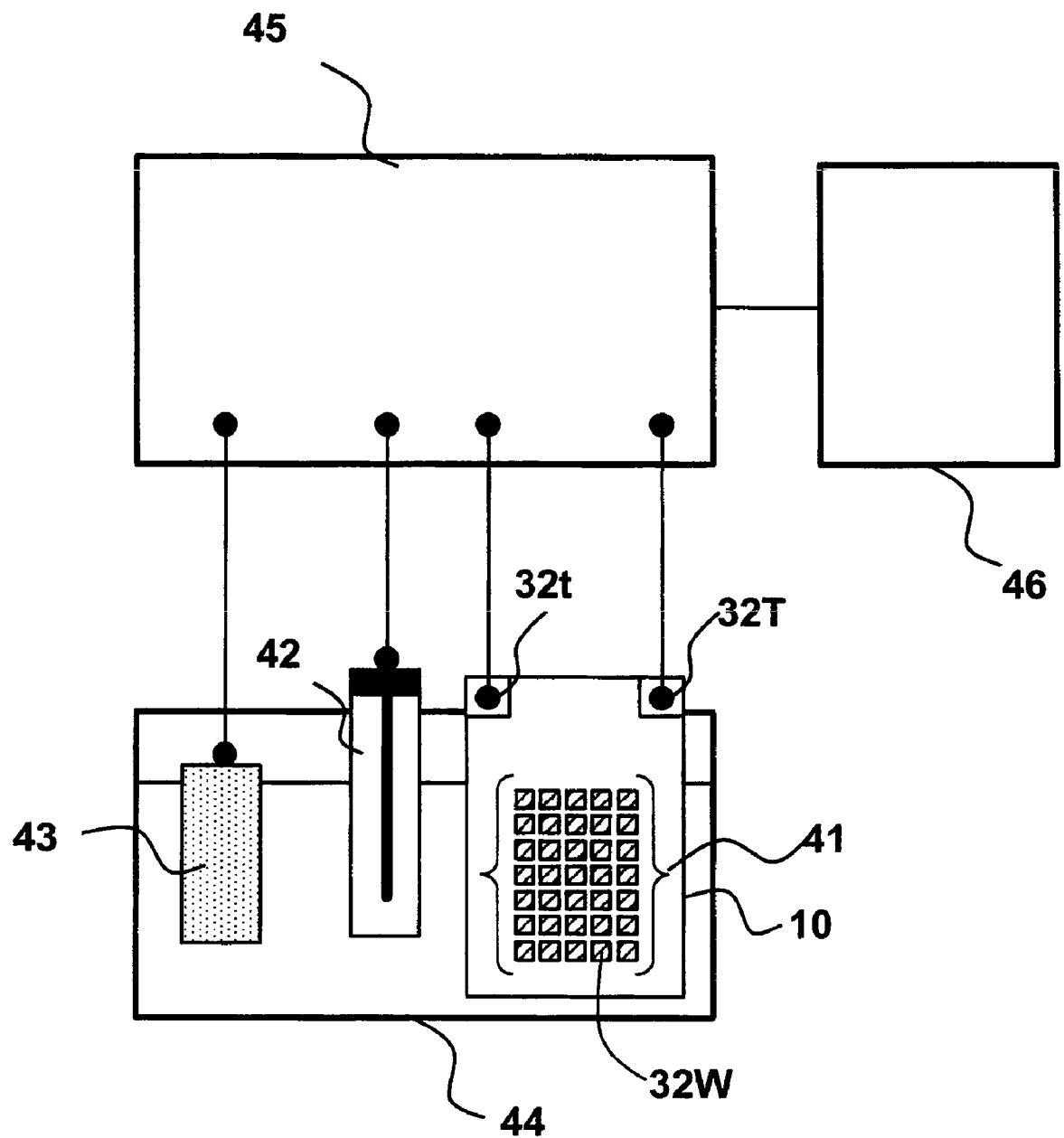
FIG. 4 shows a schematic view illustrating an apparatus for electrochemical measurements having the electrode plate for electrochemical measurements according to Embodiment 1 of the present invention.

Although the structure shown in FIG. 3 is similar to the structures illustrated in FIG. 3 and FIG. 4 in Patent Document 5, Patent Document 5 merely discloses a vessel for measuring cellular potential. Thus, an electrode plate for electrochemical measurements including an oxidation electrode and a reduction electrode; an apparatus for electrochemical measurements having this electrode plate; and a process for quantitatively determining a target substance using this electrode plate are neither disclosed nor suggested.

FIG. 4 shows an apparatus for electrochemical measurements having an electrode plate for electrochemical measurements (hereinafter, may be merely referred to as "measurement apparatus") according to Embodiment 1.

As shown in FIG. 4, the electrode plate for electrochemical measurements 10, reference electrode 42, and auxiliary electrode 43 are immersed in a sample solution filled in vessel for sample solution 44. Accordingly, these electrodes are brought into contact with the sample solution. In addition, multiple oxidation electrodes 32W are formed on the surface of the electrode plate for electrochemical measurements 10 to form assembly 41 of the oxidation electrodes 32W. Although not shown in the Figure, reduction electrodes 32w similarly form an assembly on the back face of the electrode plate for electrochemical measurements 10.

The reference electrode 44 is an electrode that serves in representing a standard of the potential applied to the electrode plate for electrochemical measurements 10. The potential shown by the reference electrode 44 in the sample solution is defined as zero, and the potentials are applied to the oxidation electrode 32W and the reduction electrode, respectively.

The auxiliary electrode 43 is an electrode for compensating the electric current so as to conform to Ampere's law in the measurement apparatus. The measurement apparatus 45 is electrically connected to the electrode plate for electrochemical measurements 10 via the oxidation electrode lead 32T and the reduction electrode lead 32t, and electrically connected to the reference electrode 42 and the auxiliary electrode 43, similarly. The electric current response that is output from the measurement apparatus 45 is recorded by recorder 46.

Explanation of Electrochemical Measuring Method

Next, a method for quantitatively determining the electronic mediator included in a sample solution is explained.

According to a process such as cyclic voltammetry, the potential to allow the oxidative reaction to proceed, and the potential to allow the reductive reaction to proceed in the electronic mediator are determined beforehand, and used for the potential value of the oxidation electrode and the potential value of the reduction electrode described later. The standard of the potential is an equilibrium potential represented by the reference electrode 42 in the sample solution. In other words, the potentials applied to the oxidation electrode 32W and the reduction electrode 32w, respectively, are a relative potential defined for the reference electrode 42 as 0 V.

After the potentials of the oxidation electrode 32W and the reduction electrode 32w are entered into the control unit 45, the measurement is started. Although explained in detail in Examples described later, specifically, positive voltage is slowly applied from 0 V to the oxidation electrode 32E. In Examples described later, the voltage applied to the oxidation electrode 32E is altered slowly and continuously from 0 V to +0.7 V. Such application is referred to as "sweeping". That is, the term "sweeping" used herein means to alter the potential continuously. In contrast, the term "applying" used herein means to alter a predetermined potential rapidly.

In this procedure, it is preferred to keep applying the same potential (0 V, in many cases) to the reduction electrode as that of the reference electrode. The speed of applying the voltage (hereinafter, may be also referred to as "sweeping speed") to the oxidation electrode 32E is generally 5 mV/sec or greater and 500 mV/sec or less. In Examples described later, the speed is 100 mV/sec.

In the foregoing description, a positive potential is swept to the oxidation electrode plate 32E, while a negative potential is applied to the reduction electrode plate 32e. However, a positive potential may be applied to the oxidation electrode plate 32E, while a negative potential may be swept to the reduction electrode plate 32e.

The electric current obtained by an oxidative reaction on the oxidation electrode 32W is detected by control unit 45 via the oxidation electrode lead 32T. Similarly, the electric current obtained by a reductive reaction on the reduction electrode 32w is detected by control unit 45 via the reduction electrode lead 32t. Thus detected electric current is output to the recorder 46, and thus the substance to be detected in the sample solution can be quantitatively determined by comparing the recorded oxidation current value with a result of measurement (calibration curve described later) of the oxidation current values of a standard sample.

It is also possible to quantitatively determine the substance to be detected in the sample solution by comparing the reduction electric current value recorded on the recorder 46 with a result of measurement of the reduction electric current of a standard sample. For this purpose, it is desirable to produce a calibration curve of the standard sample beforehand using a detection device of this Embodiment.

A method for quantitatively determining the substance to be detected in a sample solution using a calibration curve, i.e., a method of calculating the concentration of the substance to be detected in the sample solution is explained below.

A standard sample is first provided. This standard sample contains a reduced electronic mediator (herein, assumed as potassium ferrocyanide) having a known concentration. Using such a standard sample having a known concentration as a sample solution having a known concentration, relationship between the concentration of the reduced electronic mediator, and the kinetic current value measured with the apparatus for electrochemical measurements is indicated on a graph by means of the apparatus for electrochemical measurements as illustrated in FIG. 4. One example of this graph is shown in FIG. 15.

Figure 15:
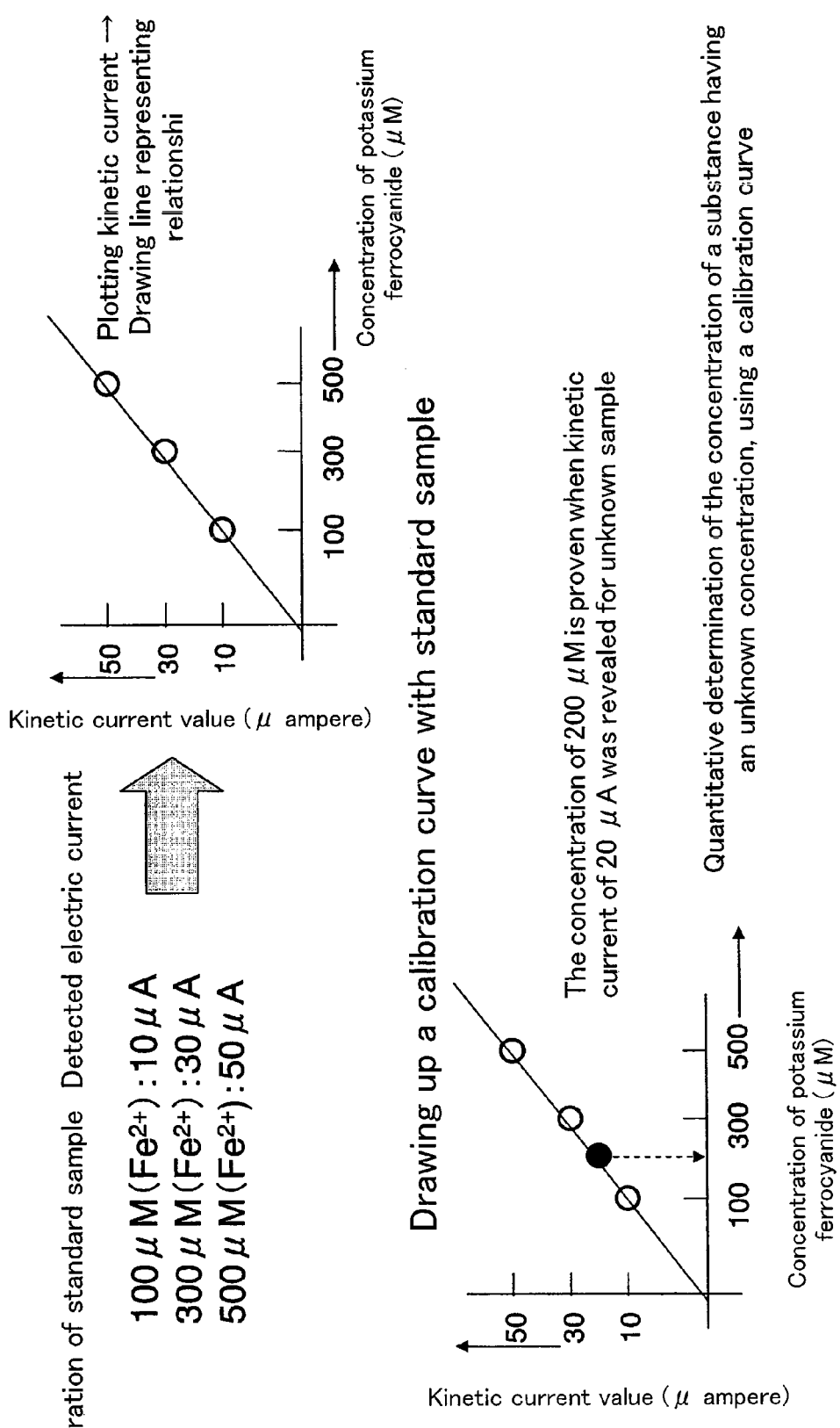
FIG. 15 shows a graph illustrating one example of a calibration curve.

As shown in FIG. 15, it is assumed herein that: the kinetic current value was 10 μA when the concentration of the reduced electronic mediator is 100 μM; kinetic current value is 30 μA when the concentration of the reduced electronic mediator is 300 μM; and the kinetic current value is 50 μA when the concentration of the reduced electronic mediator is 500 μM. These data are plotted on a graph to draw a calibration curve. Accordingly, a calibration curve is obtained from a standard sample having a known concentration.

Next, using a sample solution the concentration of which is unknown, a kinetic current value is obtained with an apparatus for electrochemical measurements as shown in FIG. 4. When the kinetic current value obtained in this procedure is 20 μA, the concentration of the reduced electronic mediator included in the sample solution (200 μM) can be revealed from the calibration curve. The amount of the target substance which is/was included in the sample solution is calculated based on this concentration of the reduced electronic mediator.

It would not be necessary to mention that production of the calibration curve, calculation of the amount of the target substance, and the like may be all carried out on a computer, in effect.

Explanation of Reference Electrode, and Auxiliary Electrode

It is also possible carry out the measurement using one counter electrode in place of the two electrodes, i.e., the reference electrode 42 and the auxiliary electrode 43. However, it is preferred to provide the reference electrode 42 and the auxiliary electrode 43 independently because the electrode reaction proceeds on the surface while the electric current flows to the counter electrode or the reference electrode to be a standard of the potential, and the potential employed as a standard of the detection device of this Embodiment varies when alteration of the concentration of the electronic mediator is enhanced as the reaction proceeds, whereby accurate measurement cannot be executed.

Therefore, it is desirable to preset the input impedance as large as possible so as not to prevent the electric current from flowing to the reference electrode 42. It is desired that the impedance value is equal to or greater than $10^6$ ohm. A silver-silver chloride electrode, a saturated calomel electrode or the like can be used for the reference electrode 42.

It is desired that the auxiliary electrode 43 has a large surface area. Preferred surface area of the auxiliary electrode 43 is ten times larger than that of the assembly 41 of the oxidation electrode 32W because when sufficient electric current cannot be flowed due to too small electrode surface area of the auxiliary electrode 43, the electric current obtained with the electrode plate for electrochemical measurements 10 does not flow enough to the control unit 45, whereby an accurate electric current value is not yielded, and additionally, the potential of the auxiliary electrode 43 greatly varies for allowing the electric current to flow, thereby leading to undesirable reactions such as electrolysis of water may be proceeded.

It is desired that a noble metal electrode that is less likely to cause an oxidation-reduction reaction of the electrode per se or a corrosion reaction is used as the auxiliary electrode 43. For example, platinum electrodes are preferred which are produced by depositing platinum black on a platinum wire to provide a great electrode area.

Embodiment 2

Figure 11:
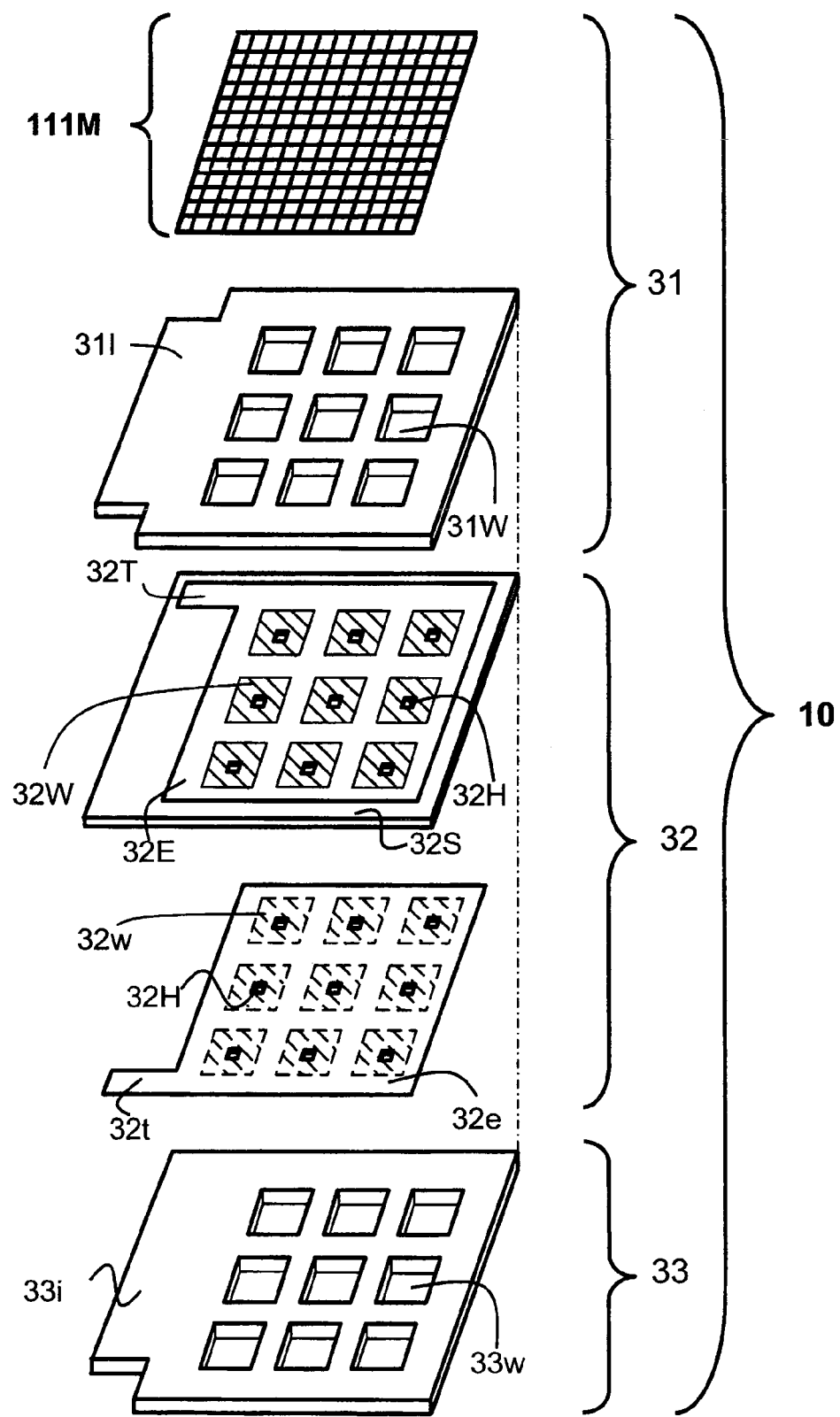
FIG. 11 shows an exploded perspective view illustrating an electrode plate for electrochemical measurements according to Embodiment 2 of the present invention.

As shown in FIG. 11, mesh filter 111M is provided on the superior face of the upper layer 31 in this Embodiment 2.

When a plasma component separated from blood is used as a sample solution used in the measurement, hardened blood clot, haemocyte components, protein components and the like which failed to separate and contaminated may block the through-hole 32H.

In order to avoid such an inexpedience, the sample solution is fed to the electrode via filtration with a filter outside the electrode system. In addition, blocking of the through-hole 32H with blood clot and the like can be prevented by forming the filter 111M having a filtrating function on the upper layer 31.

A filter (not shown in the Figure) may be also provided on the downside the lower layer 33 as needed.

Embodiment 3

Figure 13:
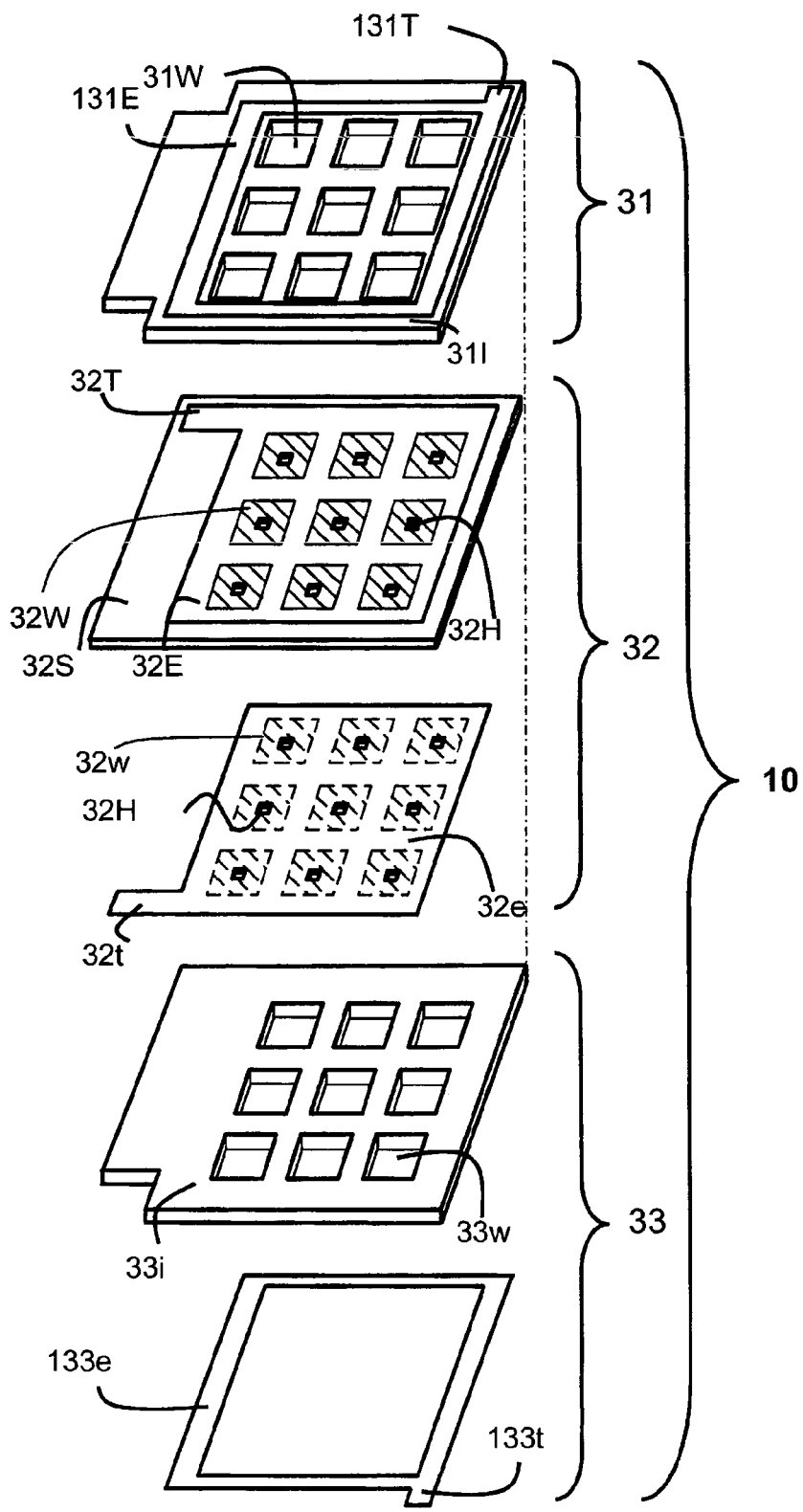
FIG. 13 shows an exploded perspective view illustrating an electrode plate for electrochemical measurements according to Embodiment 3 of the present invention.

As shown in FIG. 13, not only the oxidation electrode plate 32E and the reduction electrode plate 32e, but also the reference electrode 131E and the auxiliary electrode 133e may be formed integrally in this Embodiment 3. According to this construction, miniaturization of the apparatus is enabled since addition of the reference electrode 42 and the auxiliary electrode 43 is not required as shown in FIG. 4.

The reference electrode 131E is preferably formed on the superior face of the upper layer 31. The reference electrode 133e is preferably formed on the inferior face of the lower layer 33.

When the electrode plate for electrochemical measurements demonstrated in this Embodiment 3 is provided with the filter demonstrated in Embodiment 2 is provided, the reference electrode 131E may be provided upside the filter 111M, or to the contrary, the reference electrode 131E may be provided downside the filter 111M.

In the description of Embodiments 1 to 3, the oxidation electrode 32W is provided upside the body of the substrate 32S, while the reduction electrode 32w is provided downside the body of the substrate 32S, for the sake of convenience. Such a construction is merely illustrated for the simplification of the description. Of course, the present invention also involves the case in which the electrode plate for electrochemical measurements shown in each figure is inverted. The same is applied to the reference electrode 131E and the auxiliary electrode 133e in Embodiment 3. More specifically, the reference electrode 131E may be provided downside the lower layer 33, while the auxiliary electrode 133e may be provided upside the upper layer 31.

EXAMPLES

Hereinafter, the present invention is explained in more detail by way of Examples and Comparative Examples.

Example 1

Figure 5:
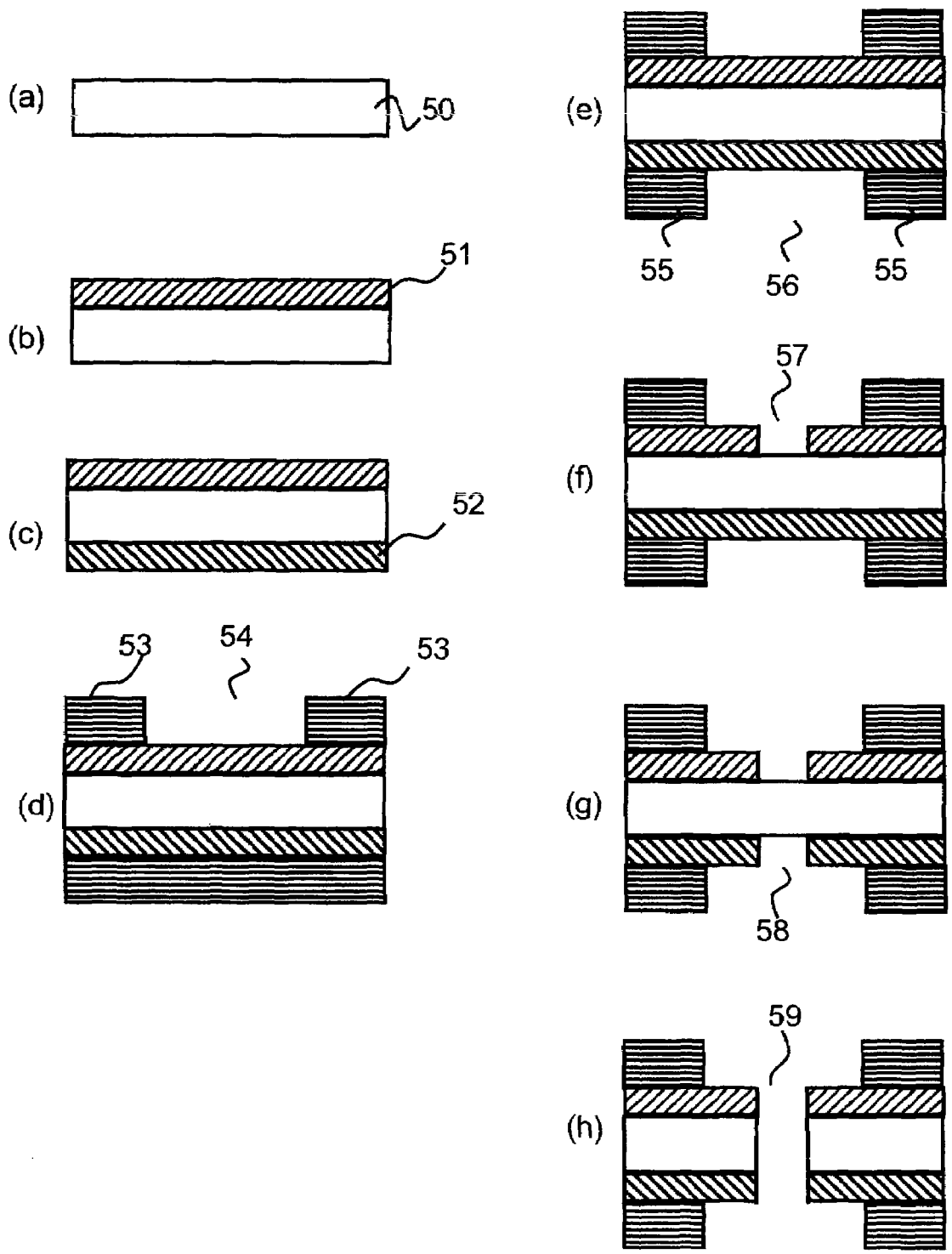
FIG. 5 shows a cross-sectional view illustrating steps of production process of the electrode plate for electrochemical measurements in Example 1 of the present invention.

FIG. 5 shows a cross-sectional view illustrating steps of production process of the electrode plate for electrochemical measurements in Example 1 of the present invention. Although just only one through-hole 32H is illustrated in FIG. 5 to FIG. 10, FIG. 12, and FIG. 14, the through-hole 32H was provided in the number as demonstrated in each Example and Comparative Example in effect.

First, as shown in FIG. 5(a) and FIG. 5(b), oxidation electrode plate 51 was formed as follows by a sputtering on the superior face of substrate 50 consisting of a silicon substrate (manufactured by Shin-Etsu Chemical Co.) having a thickness of 0.5 mm, with an $SiO_2$ film of 1 μm formed on the surface thereof.

More specifically, after the substrate 50 was mounted at a predetermined position of a sputtering apparatus (manufactured by ULVAC, Inc.), film formation was carried out with chromium and gold in this order. Specifically, sputtering was conducted at a pressure of 1.3 Pa, in an argon atmosphere, with chromium for 10 sec, and with gold for 50 sec to give an overall thickness of 130 nm. Thus, oxidation electrode plate 51 was formed.

Subsequently, as shown in FIG. 5(c), reduction electrode plate 52 was formed on the inferior face of the substrate 50 in a similar manner to the oxidation electrode plate 51.

Moreover, as shown in FIG. 5(d), upper layer 53 and upper layer opening 54 were formed on the oxidation electrode plate 51 as follows. More specifically, a photosensitive resin material (manufactured by Kayaku Microchem Co., LTD.: SU-8 2000) was applied on the superior face of the oxidation electrode plate 51 by a spin coating method to give a thickness of 2 μm. Then, after baking at 70° C. for 30 min, a mask pattern was transferred to the resin material by close contact and exposure using a chromium mask having a pattern of upper layer openings 54 for 60 sec. Thereafter, development was carried out in a developing solution at 20° C. for 300 sec, followed by water washing, and drying to form upper layer openings 54 in the shape of matrix on the upper layer 53.

The upper layer opening 54 in Example 1 is now explained in detail. The upper layer opening 54 had a shape of regular tetragon. One side of the regular tetragon had a length of 15 µm, and an area of 225 µm$^2$. The number of the upper layer openings 54 was 10,000, and the distance between the center points of the adjacent upper layer openings 54 was 18 µm.

As shown in FIG. 5(e), in a similar manner to the procedure of forming the upper layer opening 54, lower layer 55 and downside opening 56 were formed downside the reduction electrode plate 52.

Next, by etching the oxidation electrode plate 51, upside hole 57 was formed as in the following. More specifically, a resist material (manufactured by Tokyo Ohka Kogyo Co., Ltd.: TSMR-8900LB) was applied on the oxidation electrode plate 51 to give a thickness of 4 to 5 µm. The substrate 50 to which the resist was applied was placed in an oven, and a prebaking step at 100° C. for 30 min, and a postbaking step at 120° C. for 30 min were performed under each condition. Thereafter, close contact and exposure were carried out using a chromium mask having a pattern of hole 57 with a mask aligner (manufactured by MIKASA Co., LTD) for 60 sec. Next, development was carried out in a developing solution at 25° C. for 120 sec, followed by water washing, and drying to transfer the mask pattern to the resist.

Subsequently, as shown in FIG. 5(f), the substrate was placed in an argon milling apparatus, and the oxidation electrode plate 31E consisting of gold and chromium was sequentially etched under conditions of a flow rate of argon gas being 12 sccm, a pressure of 0.03 Pa, and a beam electric current of 90 mA. Accordingly, a plurality of upside holes 57 were formed on the substrate. The formed upside hole 57 was circular, having an area of 78.5 µm$^2$. The number of upside holes 57 formed on the substrate 50 was 10,000. The center of each upside hole 57 was formed so as to agree with the center of the upside opening 54.

Furthermore, as shown in FIG. 5(g), downside hole 58 was formed on the reduction electrode plate 52 in a completely similar manner to the procedure of formation of the upside hole 57 on the oxidation electrode plate 51.

Finally, as shown in FIG. 5(h), the substrate 50 having the upside hole 57 and the downside hole 58 formed thereon was placed in a reactive ion etching apparatus, and the substrate 50 was etched with the downside hole 58 as a mask pattern under conditions of a flow rate of $C_2F_6$ gas being 25 sccm, a pressure of 0.25 Pa, at 150 W for 15 min. Hence, a large number of through-holes 59 were formed on the substrate 50 (FIG. 5(h)).

Thus, the electrode plate for electrochemical measurements according to Example 1 was obtained.

Comparative Example 1

For comparison, a conventional electrode plate for electrochemical measurements was produced. Process for producing the same is presented below.

Figure 6:
FIG. 6 shows a cross-sectional view illustrating steps of production process of a conventional electrode plate for electrochemical measurements in Comparative Example 1 of the present invention.
Figure 6:
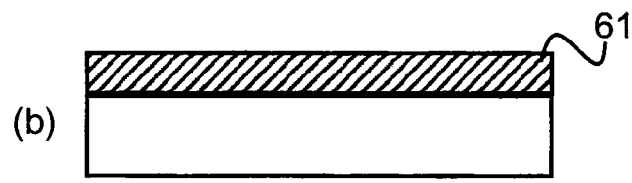
Figure 6:
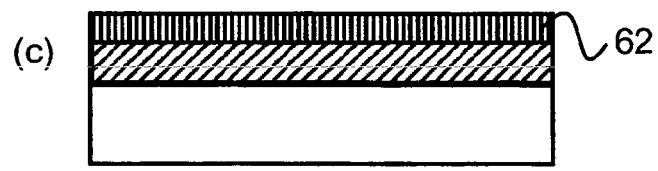
Figure 6:
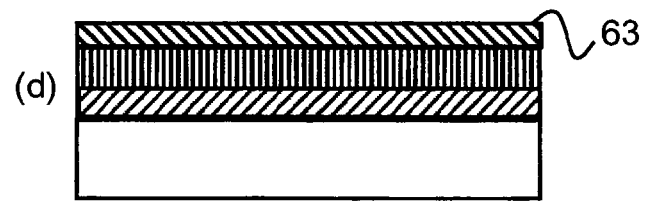
Figure 6:
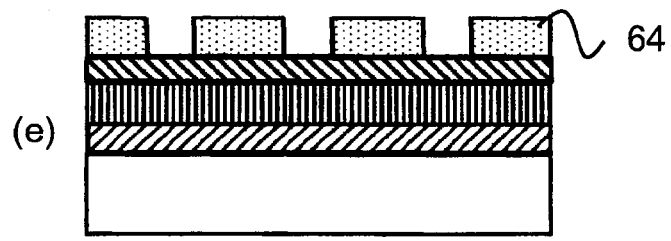
Figure 6:
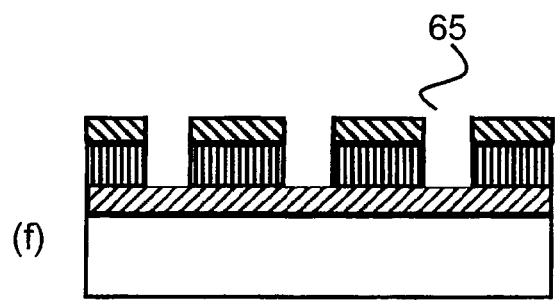

As shown in FIG. 6, bottom electrode 61 consisting of chromium and gold was formed on the superior face of a silicon substrate (manufactured by Shin-Etsu Chemical Co.) as substrate 60 having a thickness of 0.5 mm having an $SiO_2$ film of 1 µm on the surface thereof. The film formation conditions were the same as those shown in FIG. 5(b).

Next, as shown in FIG. 6(c), insulating layer 62 having a thickness of 430 nm and consisting of $SiO_2$ was deposited onto the superior face of the bottom electrode 61 using a plasma CVD apparatus (manufactured by ULVAC, Inc.).

The film formation conditions involved a flow rate of silane gas being 10 sccm, a flow rate of $N_2O$ gas being 200 sccm, a pressure of 80 Pa, a power of 50 W, and a substrate temperature of 300° C.

Furthermore, as shown in FIG. 6(d), surface electrode 63 consisting of chromium and gold was formed. The film formation conditions were the same as those shown in FIG. 5(b)

Next, as shown in FIG. 6(e), resist material 64 having a thickness of 2 to 3 µm was applied on the superior face of the surface electrode 63, followed by development, water washing, and drying to transfer the mask pattern to the resist 64. The conditions of resist and resist pattern formation employed were the same as those in description in connection with FIG. 5(d).

Thereafter, as shown in FIG. 6(f), micropore 65 was formed. A part on which the resist 64 was not formed, i.e., a part corresponding to the exposed surface electrode 63 was etched sequentially using an argon milling apparatus. The conditions of the argon milling involved a flow rate of argon gas being 12 sccm, pressure of 0.03 Pa, and beam electric current of 90 mA.

Finally, a large number of micropores 65 were formed on the insulating layer 62 using a reactive ion etching apparatus. The conditions of the reactive ion etching involved a flow rate of $C_2F_6$ gas being 25 sccm, a pressure of 0.25 Pa, and 150 W.

The micropore 65 in Comparative Example 1 is now explained in detail. The micropore 65 had a circular shape. Its diameter was 10 µm, with the area of 78.5 µm$^2$. The number of the micropores 65 was 10,000, and the distance between the center points of the adjacent micropores 65 was 70 µm. The micropore 65 did not penetrate through the bottom electrode 61 and the substrate 60 as shown in FIG. 6(f).

Electrochemical Measurement According to Example 1 and Comparative Example 1

Using the electrode plate for electrochemical measurements according to Example 1 and Comparative Example, an apparatus for electrochemical measurements was assembles as shown in FIG. 4, and quantitative determination and evaluation of electronic mediator was performed.

A sample solution was prepared by adding 1 mM potassium ferrocyanide and 1 mM potassium ferricyanide (2 mM in total) to an aqueous solution containing 50 mM supporting electrolyte (potassium chloride).

A silver/silver chloride electrode (manufactured by BAS Inc.) was used as a reference electrode. Hereinbelow, the potential of the oxidation electrode and the potential of the reduction electrode are all the potential for this silver/silver chloride electrode used as a reference electrode.

The electrode plate for electrochemical measurements according to Example 1 was connected to a bipotentiostat (manufactured by CH Instruments: ALS740A) via a lead wire. After setting the potential of the oxidation electrode plate 51 to be 0 V, the potential of the reduction electrode plate 52 to be 0 v, and sweeping speed of the potential of the oxidation electrode plate 51 to be 100 mV/s, kinetic current was measured which flowed to the oxidation electrode plate 51 until the potential of the oxidation electrode plate 51 finally became +0.7 V, with a cyclic voltammetry method. Thus observed reaction is an oxidative reaction of potassium ferrocyanide represented by the formula 1.

A stationary electric current was observed during the potential of the oxidation electrode plate 51 was altered from +0.6 to +0.7 V. The kinetic current at +0.7 V was 39.8 µA.

In a similar manner, using the electrode plate for electrochemical measurements according to Comparative Example 1, the potential of the bottom electrode 2 that functions as an oxidation electrode was swept from 0 to +0.7 V at a sweeping speed of 100 mV/s. The potential of the surface electrode 4 that functions as a reduction electrode was preset to be 0 V.

As a result, an oxidation current which would flow upon the oxidative reaction of potassium ferrocyanide represented by the formula 1 was observed also on the bottom electrode. A stationary electric current was observed during the potential of the bottom electrode 61 was altered from +0.6 to +0.7 V. The kinetic current at +0.7 V was 22.5 μA.

$$Fe(CN)_6^{-4} \rightarrow Fe(CN)_6^{-3} + e^-$$ [formula 1]

Experimental results of Example 1 and Comparative Example 1 are summarized in Table 1 below.

TABLE 1

| | Stationary state electric current value (μA) |
|---|---|
| Example 1 | 39.8 |
| Comparative Example 1 | 22.5 |
| Comparative Example 2 | 20.7 |
| Example 2 | 53.2 |
| Example 3 | 64.8 |
| Example 4 | 42.6 |

When considered by applying to the explanatory drawing of a self-induced redox cycle shown in FIG. 2, it is believed that the electric current value of the oxidative reaction was increased efficiently since the entire potassium ferrocyanide was oxidized only on the microelectrode 21 in Example 1, but to the contrary, potassium ferrocyanide which had been oxidized on the macroelectrode 22b at a part far from the microelectrode in Comparative Example 1 was not employed in the oxidative reaction on the microelectrode 21.

In the electrode plate for electrochemical measurements of this Example, a large number of microelectrode pairs having the same shape and the same area were arranged on the substrate. Thus, it is believed that even reaction area was achieved in each electrode pair, whereby occurrence of the reaction of potassium ferrocyanide on the macroelectrode as described above could be avoided, or significantly decreased. Accordingly, it is assumed that efficient redox cycle reaction proceeded between both electrodes.

In addition, the bottom electrode 61 that constructs the microelectrode of Comparative Example 1, and time dependency of the oxidation current achieved by applying a potential of +0.4 V to the oxidation electrode plate 51 that constructs the electrode for electrochemical measurements of Example 1 was evaluated. The potential of the reduction electrode plate 52 of Example 1, and the potential of the surface electrode 63 of Comparative Example 1 were kept to be 0 V.

As a result, the oxidation current value of Example 1 reached to the stationary state in 6 sec, but 26 sec was required until the oxidation current value reached to the stationary state in Comparative Example 1 (Table 2). It is assumed from these results that a longer time period until reaching to the stationary state was necessary due to a larger area of the top electrode in comparison with the bottom electrode of Comparative Example 1, but to the contrary, the stationary state was immediately attained between both electrodes since the oxidation electrode of Example 1 formed an electrode pair with the reduction electrode having the same area.

TABLE 2

| | Time period required until reaching to stationary state |
|---|---|
| Example 1 | 6 |
| Comparative Example 1 | 26 |
| Comparative Example 2 | 35 |
| Example 2 | 10 |
| Example 3 | 9 |
| Example 4 | 15 |

From the foregoing results, advantages of the electrode plate for electrochemical measurements of this Example were found.

Comparative Example 2

In order to verify the influences of the areas of the upper layer opening 54 and the lower layer opening 56 in Example 1 exerted on evaluation of the quantitative determination of the electronic mediator, an electrode plate for electrochemical measurements according to Comparative Example 2 was produced with the following process.

Fundamental process for production is identical with that shown in FIG. 5, only the different points are explained below. In Comparative Example 2, one side of upper layer opening 54 of the regular tetragon had a length of 1,000 μm, and an area of 1,000,000 μm². The number of the upper layer openings 54 was 10, and the distance between the center points of the adjacent upper layer openings 54 was 1,500 μm.

Using this electrode, the kinetic current was measured with a cyclic voltammetry method in a similar manner to Example 1, the stationary electric current was observed during the potential of the oxidation electrode plate 51 was altered from +0.6 to +0.7 V. The kinetic current at +0.7 V was 20.7 μA. Similarly, time dependency of the oxidation current was also evaluated. A time period of 35 sec was required until the electric current that flowed the oxidation electrode of Comparative Example 2 reached to the stationary state (Table 2).

It is assumed that when the area of the opening provided on the electrode plate for electrochemical measurements of the present invention was as large as 1,000,000 μm², a part close to and a part far from the oxidation electrode were present on the reduction electrode as shown in FIG. 2; therefore, the reductant to be oxidized on the oxidation electrode was reacted on the reduction electrode, leading to failure in occurrence of efficient reaction on the oxidation electrode.

Example 2

Figure 7:
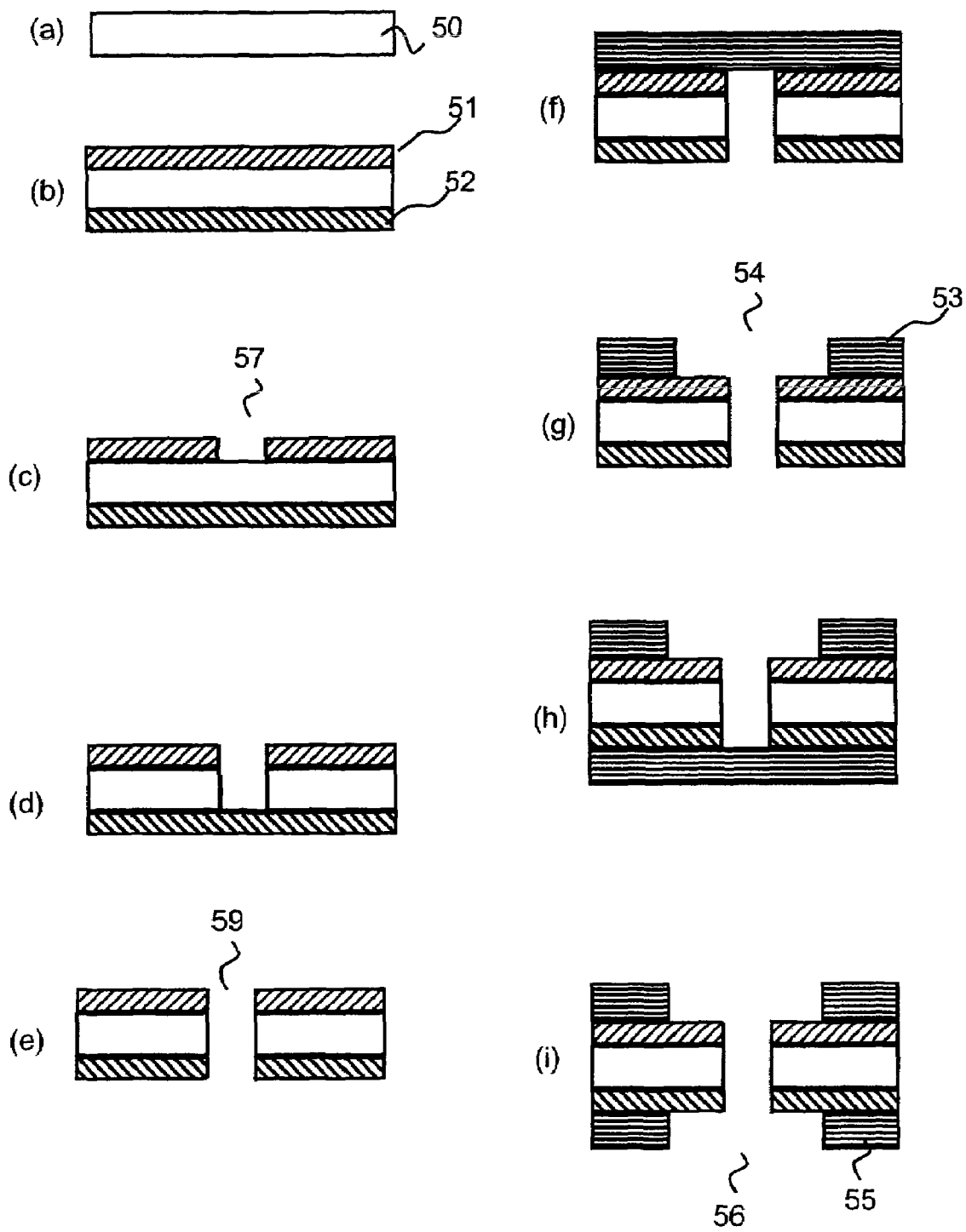
FIG. 7 shows a cross-sectional view illustrating steps of production process of the electrode plate for electrochemical measurements in Example 2 of the present invention.

FIG. 7 shows a cross-sectional view illustrating steps of production process of the electrode plate for electrochemical measurements in Example 2 of the present invention. Similar process to Example 1 was carried out until the step of forming the oxidation electrode plate 51 and the reduction electrode plate 52 (steps a to c).

Next, according to the process employed in Example 1, oxidation electrode plate 51, substrate 50, and reduction electrode plate 52 were sequentially etched to form through-holes 59 having a cross sectional area of 100 μm² in the number of 5,000 such that even intervals are provided (steps c to e).

Next, upper layer 53 and upper layer opening 54 were formed upside the oxidation electrode plate 51. In addition, lower layer 55 and lower layer opening 56 were formed on the lower layer of the reduction electrode plate 52.

As the material for the upper layer 53 and the lower layer 55, a dry film resist having a thickness of 5 μm (manufactured by Asahi Kasei Corporation, Sunfort) was used. The upper layer openings 54 and the lower layer openings 56 were formed in the number of 5,000, respectively. These openings had a cross sectional area of 900 μm². The method of the formation of the upper layer opening and the lower layer opening was similar to that in Example 1 (steps f to i)).

According to the steps described above, the electrode plate for electrochemical measurements of this Example was obtained.

Using the electrode plate for electrochemical measurements of this Example, a similar test to Example 1 was performed. As shown in Table 1, the electric current value observed on the oxidation electrode 51 was greater than that of the bottom electrode 61 in Comparative Example 1. Furthermore, as shown in Table 2, the time period required until the electric current value observed on the oxidation electrode 51 reached to the stationary state was 10 sec, which was shorter than that of Comparative Example 1.

From the foregoing results, advantages of the electrode plate for electrochemical measurements of this Example were found.

Example 3

Figure 8:
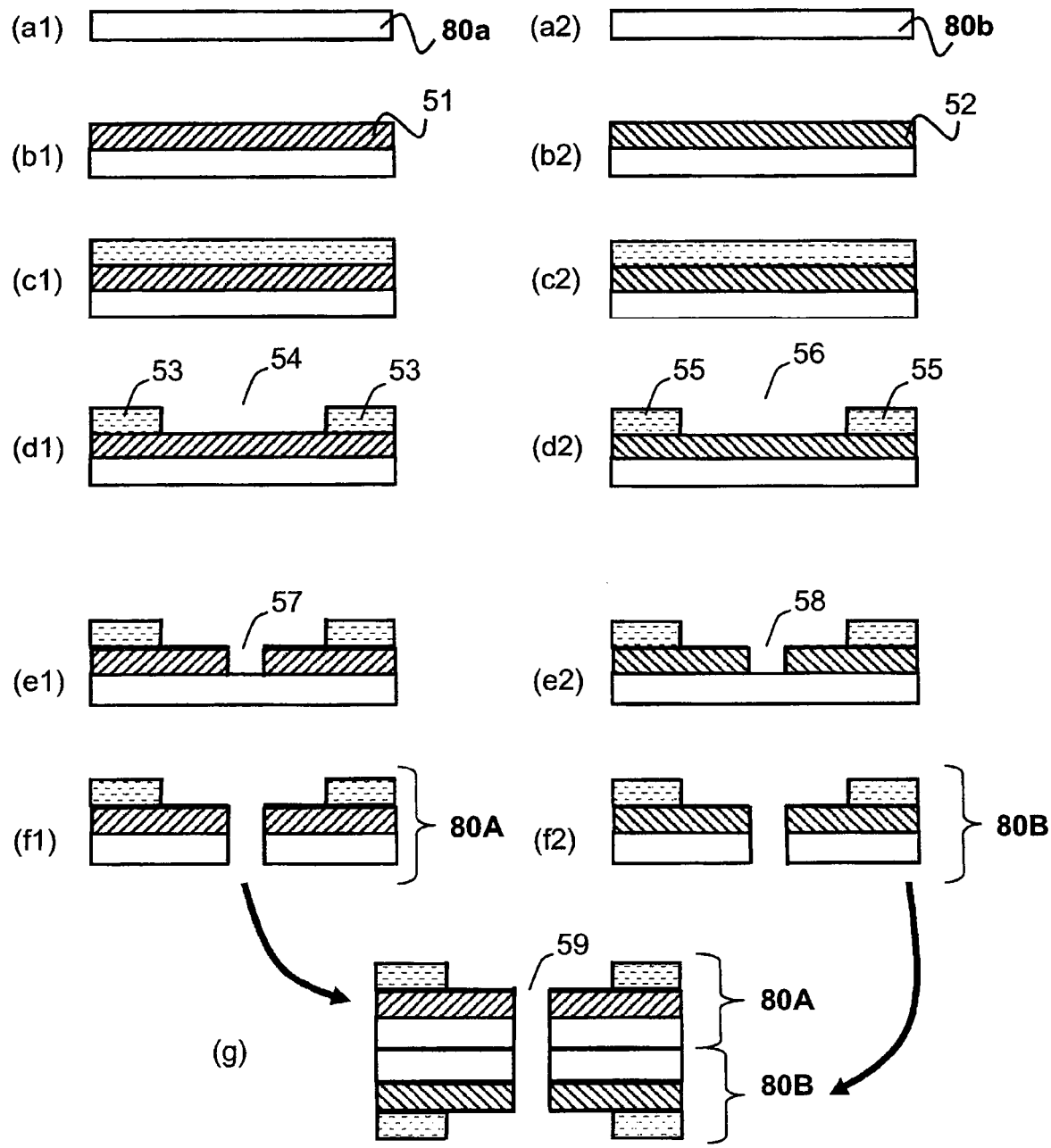
FIG. 8 shows a cross-sectional view illustrating steps of production process of the electrode plate for electrochemical measurements in Example 3 of the present invention.

FIG. 8 shows a cross-sectional view illustrating steps of production process of the electrode plate for electrochemical measurements in Example 3. In this Example, a similar process to Example 1 was performed including: the steps of forming oxidation electrode plate 51 and reduction electrode plate 52 (steps b1 and b2), the steps of forming the upper layer and the lower layer (steps c1 and c2), the steps of forming the upper layer opening and the lower layer opening (steps d1 and d2), the steps of forming the upside through-hole and the downside through-hole (steps e1, e2, f1 and f2). As a result, substrate having an oxidation electrode formed thereon BOA, and substrate having a reduction electrode formed thereon 80B were formed.

The electrode plate for electrochemical measurements of this Example was obtained by laminating the two substrates on each inferior face (step g). The upper layer openings 54 and the lower layer openings 56 had a cross sectional area of 900 μm², and they were formed in the number of 1,000 with being evenly spaced. The through-holes 59 had a cross sectional area of 314 μm².

Using the electrode for electrochemical measurements of this Example, a similar test to Example 1 was performed. Consequently, similar results to Example 1 as shown in Table 1 were obtained. From the foregoing results, advantages of the electrode plate for electrochemical measurements of this Example were found.

Example 4

Figure 9:
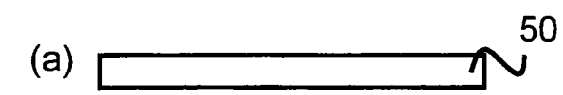
FIG. 9 shows a cross-sectional view illustrating steps of production process of the electrode plate for electrochemical measurements in Example 4 of the present invention.
Figure 9:
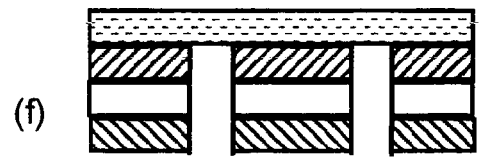
Figure 9:
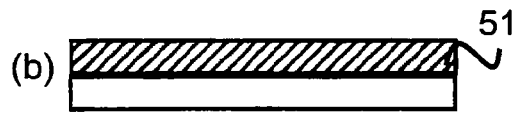
Figure 9:
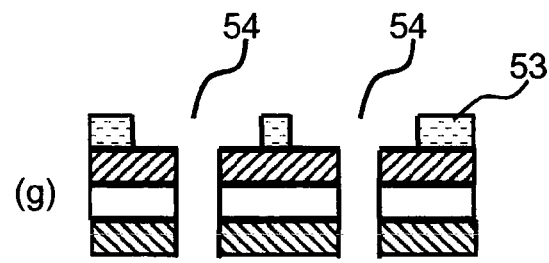
Figure 9:
Figure 9:
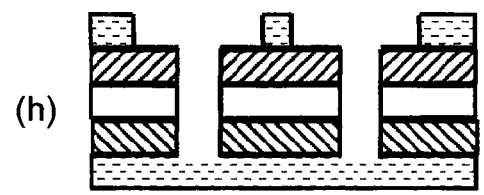
Figure 9:
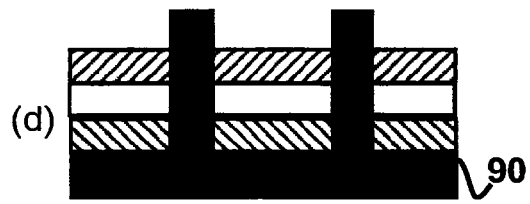
Figure 9:
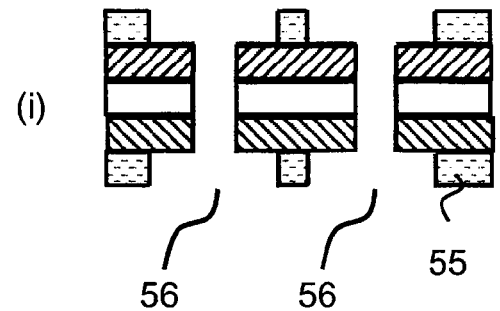
Figure 9:
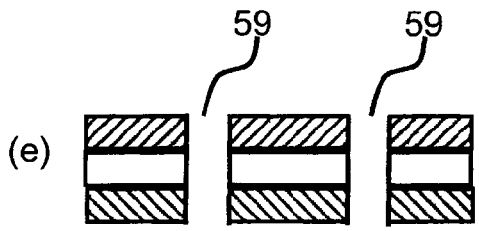

FIG. 9 shows a cross-sectional view illustrating steps of production process of the electrode plate for electrochemical measurements in Example 4. A thermosetting phenol resin material (PM-8200, manufactured by Sumitomo Bakelite Co., Ltd.) having a thickness of 0.5 mm was used as the insulative substrate 50. Oxidation electrode plate 51 and reduction electrode plate 52 were formed on the substrate (steps a to c).

Next, the substrate having the electrode plate formed thereon was subjected to through-hole formation processing. Mold 90 was heated to 160° C., and completely penetrated through from the inferior face of the reduction electrode plate 52 to the superior face of the oxidation electrode 51, which was kept at the same temperature for 10 min (step d). Subsequently, it was gradually cooled to room temperature at a rate of 5° C./min, and kept at room temperature for 10 min. Then, the mold 90 was removed to form through-holes 59 in the number of 1,000. These through-holes had a cross sectional area of 314 μm² (step e).

Next, a similar process to Example 2 was performed to form upper layer 53 and upper layer openings 54, and lower layer 55 and lower layer openings 56 in the number of 1,000 (steps f to i). These openings had an area of 6,400 μm². Accordingly, the electrode plate for electrochemical measurements of this Example was obtained.

Using the electrode plate for electrochemical measurements of this Example, a similar test to Example 1 was performed. Consequently, similar results to Example 1 as shown in Table 1 were obtained. From the foregoing results, advantages of the electrode plate for electrochemical measurements of this Example were found.

Example 5

Figure 10:
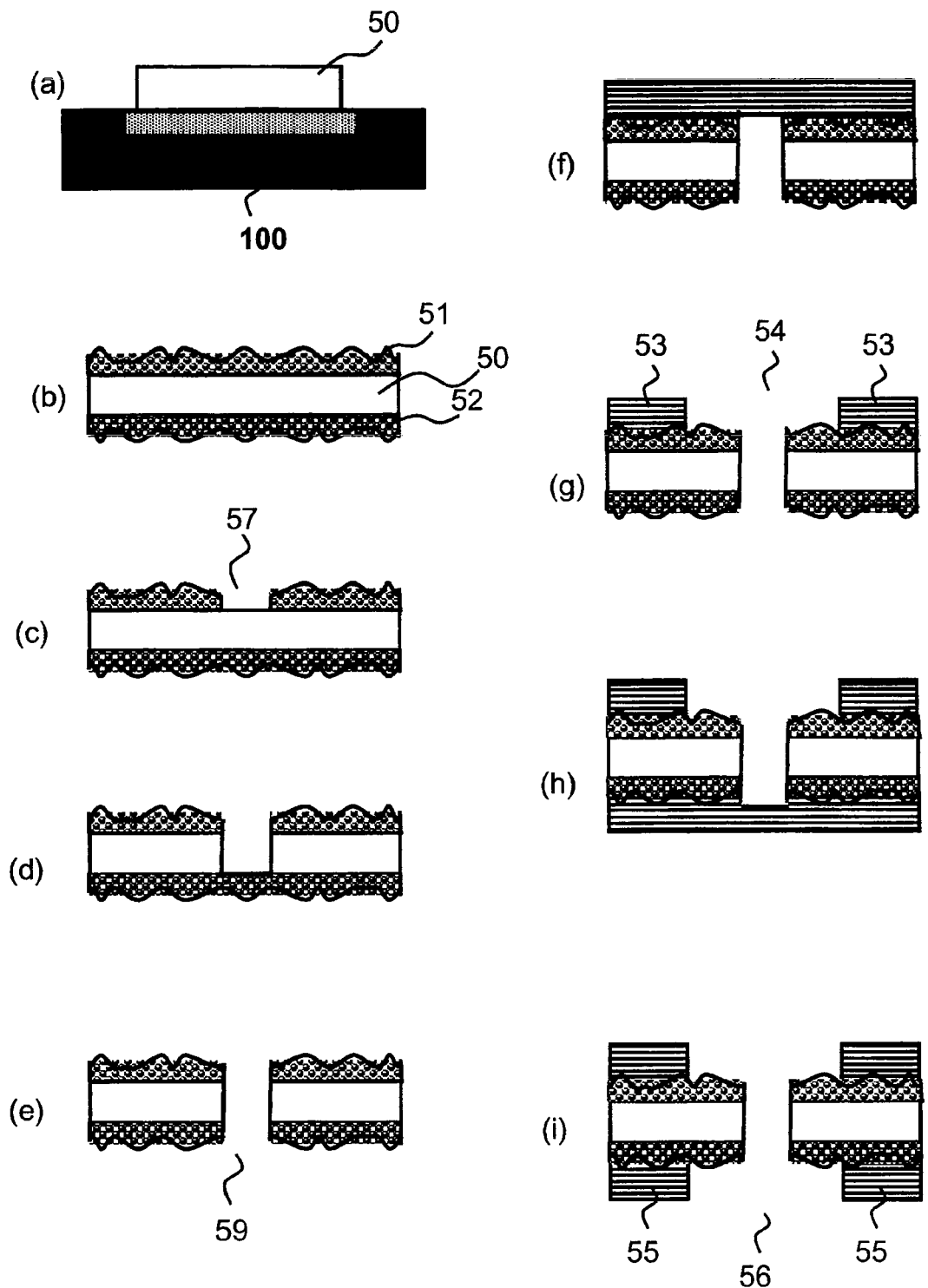
FIG. 10 shows a cross-sectional view illustrating steps of production process of the electrode plate for electrochemical measurements in Example 5 of the present invention.

FIG. 10 shows a cross-sectional view illustrating steps of production process of the electrode plate for electrochemical measurements in Example 5. Substrate 50 employed was a silicon substrate (manufactured by Shin-Etsu Chemical Co.) having a diameter of 4 inches and a thickness of 0.5 mm, with an SiO₂ film of 1 μm formed on the surface thereof.

A titanium film was formed on both entire faces to give a thickness of 10 nm. Next, the inferior face was fixed on work table 100 of a spin coater by vacuum contact (step a). Porous Chuck (manufactured by Yoshioka Seiko Co., Ltd.) was employed as work table 100. The contact part was formed with sintered porous alumina.

A dispersion liquid of palladium particles having a diameter of 5 nm (solvent: hexane) was applied onto the entire superior face of the substrate 50 to give a thickness of 500 nm. Then, baking was conducted in an electric furnace equipped with a ventilation system at 300° C. for 3 hrs to form oxidation electrode 51. Subsequently, the dispersion liquid of palladium particles was applied similarly onto the inferior face, which was then baked to form reduction electrode 52 (step b).

Next, a similar process to Example 1 was performed to form through-holes 59 in the number of 1,000. The through-holes had a cross sectional area of 1,000 μm² (steps c to e).

Subsequently, a similar process to Example 2 was performed to form upper layer 53 and upper layer openings 54, and lower layer 55 and lower layer openings 56 in the number of 2,500 μm². These openings had a cross sectional area of 1,000 μm² (steps f to i). According to the steps described above, the electrode plate for electrochemical measurements of this Example was obtained.

The oxidation electrode surface and the reduction electrode surface of thus resulting electrode plate for electrochemical measurements were observed with an atom force microscope. As a result, a structure in which grains having a diameter of approximately 50 nm were aggregated was ascertained on the oxidation electrode surface and the reduction electrode surface. In contrast, on the palladium electrode surface produced by the process for forming a film, only a shape that reflected polishing flaws generated in polishing of the substrate was observed, with no grain structure found.

Then, the surface area of the oxidation electrode on the electrode plate for electrochemical measurements of this Example was estimated. Assuming that the surface of the substrate 50 were simply covered with hemispheres of palladium particles having a diameter of 50 nm, sum total of the surface area of the hemispheres was about 30 times greater than the geometrical area. Since the electrode surface produced by the process for forming a film was almost even, the area almost agrees with the geometrical area. Therefore, it was proven that the electrode plate for electrochemical measurements of this Example had a larger area of the electrode than that of the electrode produced by the process for forming a film. This leads to increase in reaction area of the electrode. Accordingly, it was revealed that the electrode plate for electrochemical measurements of the present invention has preferable properties.

Next, steps of producing the electrode plate for electrochemical measurements of Embodiment 2 are described with reference to FIG. 12.

Example 6

Figure 12:
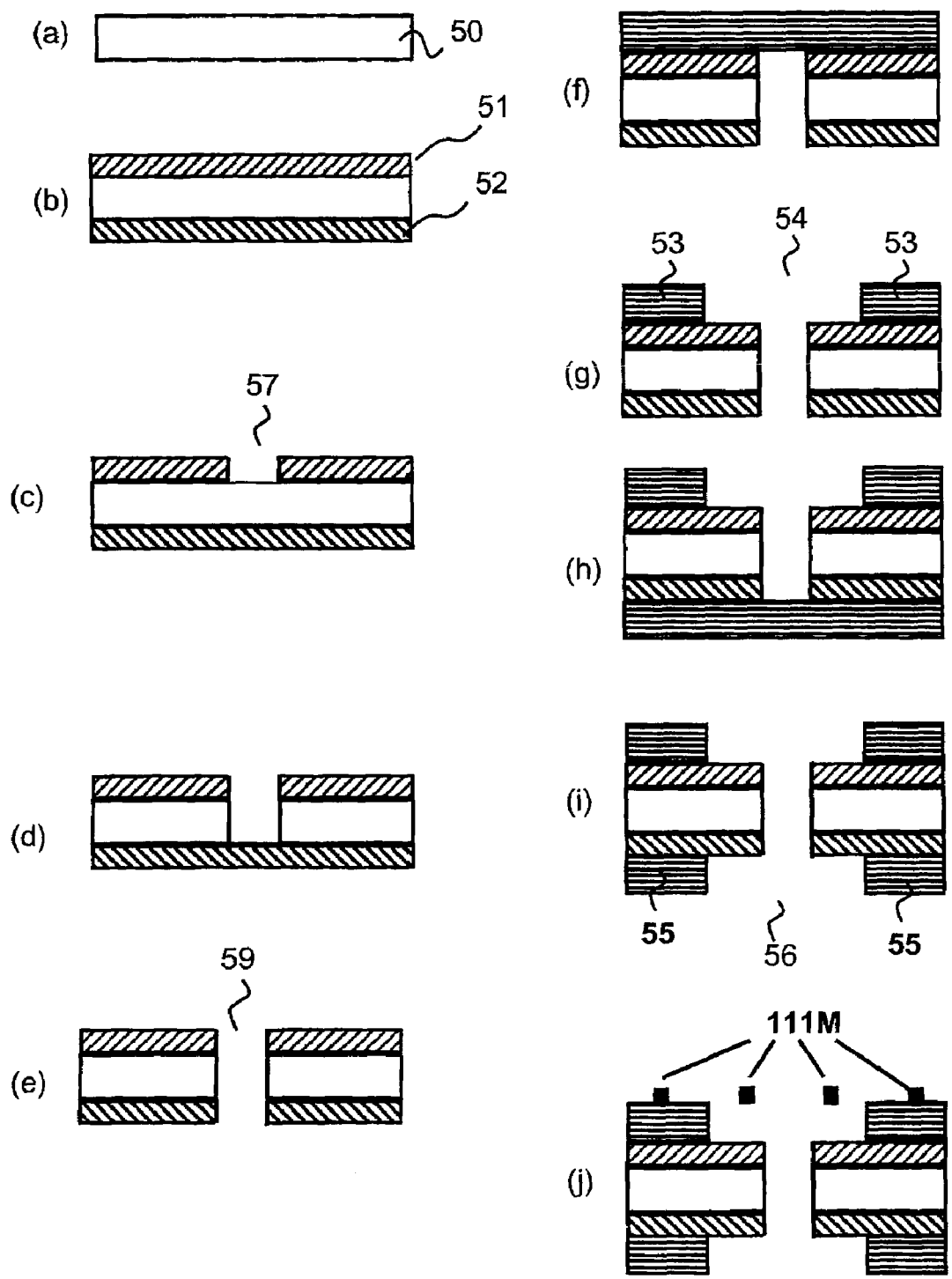
FIG. 12 shows a cross-sectional view illustrating steps of production process of the electrode plate for electrochemical measurements in Example 6 of the present invention.

FIG. 12 shows a cross-sectional view illustrating steps of production process of the electrode plate for electrochemical measurements in Example 6. Oxidation electrode plate 51, reduction electrode plate 52, upper layer 53, upper layer opening 54, lower layer 55, lower layer opening 56, and through-hole 59 were formed on the substrate 50 with the process of Example 1. The through-holes had a cross sectional area of 100 $\mu m^2$, and the openings had a cross sectional area of 10,000 $\mu m^2$, and they were formed in the number of 2,500, respectively (steps a to i).

Finally, after a filter 113M with a pore size of 42 μm composed of borosilicate fiber glass (manufactured by Nihon Millipore Ltd.) was cut into a certain size, it was fixed on the upper layer 53 using a silicon adhesive (step j).

According to the steps described above, the electrode plate for electrochemical measurements of this Example was obtained.

As a result of inserting plasma components in blood into the electrode plate for electrochemical measurements of this Example, the haemocyte component, the protein component, and blood clot which had not been separated were trapped on the filter 113M, plasma components alone were fed to the lower layer opening via the upper layer opening 54, and through-hole 59. To the contrary, the electrode plate for electrochemical measurements having the same shape but having no filter 113M formed was partially blocked with the blood clot, leading to failure in functioning of the through-hole 59. These results were confirmed by visual observation. From the foregoing results, advantages of the electrode plate for electrochemical measurements of this Example were found.

Next, steps of producing the electrode plate for electrochemical measurements of Embodiment 3 are described with reference to FIG. 14.

Example 7

Figure 14:
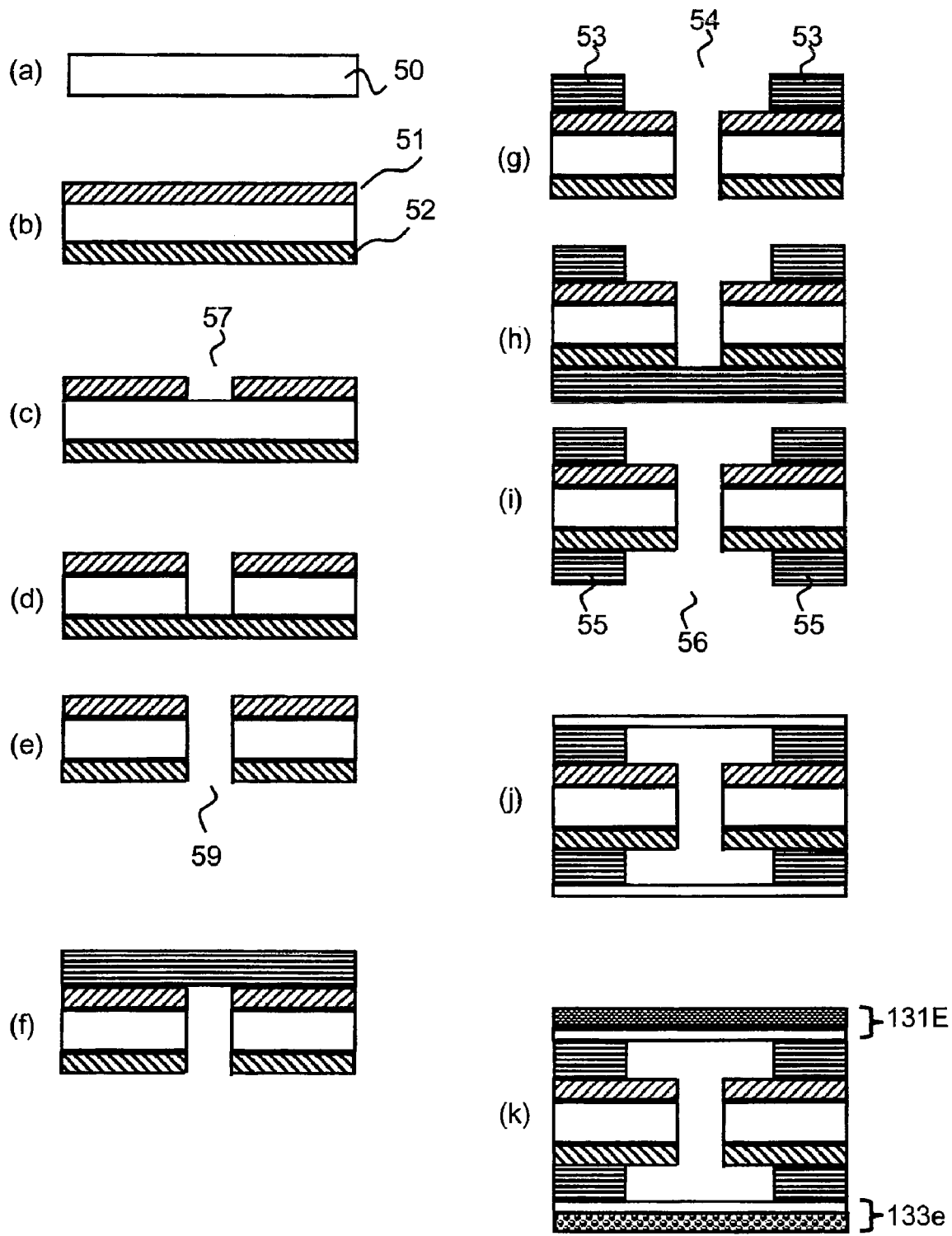
FIG. 14 shows a cross-sectional view illustrating steps of production process of the electrode plate for electrochemical measurements in Example 7 of the present invention.

FIG. 14 shows a cross-sectional view illustrating steps of production process of the electrode plate for electrochemical measurements in Example 7. Oxidation electrode plate 51, reduction electrode plate 52, upper layer 53, upper layer opening 54, lower layer 55, lower layer opening 56, and through-hole 59 were formed on the substrate 50 with the process of Example 1. The through-holes had a cross sectional area of 100 $\mu m^2$, and the openings had a cross sectional area of 2,500 $\mu m^2$, and they were formed in the number of 5,000, respectively (steps a to i).

Next, a metal mask was covered over the upper layer 53 and the lower layer 55 to form a film of platinum to give a thickness of 100 nm (j). After removing the metal mask, a silver-silver chloride ink (manufactured by BAS Inc.) was applied on the platinum thin film which had been formed on the upper layer 53, leaving the part of the lead. Thereafter, drying in an electric furnace at 40° C. for 30 min was carried out to obtain reference electrode 131E. Subsequently, platinum powders (manufactured by Tanaka Kikinzoku Kogyo) having a mean particle diameter of 1.0 to 10.0 μm were dispersed in ethanol to produce a slurry. Thus produced slurry was applied on the platinum thin film which had been formed on the lower layer 55, leaving the part of the lead, and was dried to obtain auxiliary electrode 133e. According to the steps described above, the electrode plate for electrochemical measurements of this Example was obtained.

Using the electrode plates for electrochemical measurements produced in this Example and in Comparative Example 1, apparatuses for electrochemical measurements were assembled, respectively. The electrode plate for electrochemical measurements of this Example had a thickness of approximately 0.5 mm, while that of Comparative Example 1 had a thickness of approximately 5 cm since a reference electrode and an auxiliary electrode were externally incorporated. Hence, the amount of the sample solution used in the measurement increased by several thousand times. This suggests that a construction suitable as an electrode for a variety of sensors on which miniaturization has been demanded could be achieved by integrally forming electrodes required for the measurement on an electrode plate. Therefore, it was proven that the electrode plate for electrochemical measurements of this Example is suitable as an electrode for small sensors.

From the foregoing description, many modifications and other embodiments of the present invention are apparent to persons skilled in the art. Accordingly, the foregoing description should be construed merely as an illustrative example, which was provided for the purpose of teaching best modes for carrying out the present invention to persons skilled in the art. Details of the construction and/or function of the present invention can be substantially altered without departing from the spirit thereof.

INDUSTRIAL APPLICABILITY

The electrode plate for electrochemical measurements of the present invention has a high redox cycle effect, and is useful as an electrode that constructs a sensing device of minor components such as biological substances, as typified by glucose sensors. In addition, it can be also adopted for applications of electrodes that construct detectors of chromatography, and the like.

What is claimed is:

1. An electrode plate for electrochemical measurements comprising:
   a substrate made of an insulator,
   an upper layer made of an insulator provided on an upper face of the substrate, and
   a lower layer made of an insulator provided on a lower face of the substrate, wherein:
   the substrate comprises
   a plurality of oxidation electrodes sandwiched between the upper face of the substrate and the upper layer, and
   a plurality of reduction electrodes sandwiched between the lower face of the substrate and the lower layer;
   the upper layer comprises a plurality of upper layer openings;
   each of the oxidation electrodes is exposed from each of the upper layer openings;
   the lower layer comprises a plurality of lower layer openings;

each of the reduction electrodes is exposed from each of the lower layer openings;

the substrate is provided with a plurality of through-holes that penetrate from an upper face of each of the oxidation electrodes to a lower face of each of the reduction electrodes;

each of the upper layer openings has the same area with an area of each of the lower layer openings;

each of the upper layer openings has an area of equal to or less than 10,000 $\mu m^2$, and each of the lower layer openings has an area of equal to or less than 10,000 $\mu m^2$.

2. The electrode plate for electrochemical measurements according to claim 1, wherein each of the upper layer openings has an area of equal to or greater than 225 $\mu m^2$, and each of the lower layer openings has an area of equal to or greater than 225 $\mu m^2$.

3. The electrode plate for electrochemical measurements according to claim 1, wherein the through-hole has a cross sectional area of 1 $\mu m^2$ or greater and 2,500 $\mu m^2$ or less.

4. The electrode plate for electrochemical measurements according to claim 1, wherein the lower layer has a thickness of 5 $\mu m$ or greater and 100 $\mu m$ or less.

5. An apparatus for electrochemical measurements comprising a reference electrode, an auxiliary electrode and an electrode plate for electrochemical measurements, or a counter electrode and an electrode plate for electrochemical measurements, the electrode plate for electrochemical measurements comprising a substrate made of an insulator, an upper layer made of an insulator provided on an upper face of the substrate, and a lower layer made of an insulator provided on a lower face of the substrate, wherein:

the substrate comprises a plurality of oxidation electrodes sandwiched between the upper face of the substrate and the upper layer, and a plurality of reduction electrodes sandwiched between the lower face of the substrate and the lower layer;

the upper layer comprises a plurality of upper layer openings;

each of the oxidation electrodes is exposed from each of the upper layer openings;

the lower layer comprises a plurality of lower layer openings;

each of the reduction electrodes is exposed from each of the lower layer openings;

the substrate is provided with a plurality of through-holes that penetrate from an upper face of each of the oxidation electrodes to a lower face of each of the reduction electrodes;

each of the upper layer openings has the same area with an area of each of the lower layer openings;

each of the upper layer openings has an area of equal to or less than 10,000 $\mu m^2$, and each of the lower layer openings has an area of equal to or less than 10,000 $\mu m^2$.

6. The apparatus for electrochemical measurements according to claim 5, wherein each of the upper layer openings has an area of equal to or greater than 225 $\mu m^2$, and each of the lower layer openings has an area of equal to or greater than 225 $\mu m^2$.

7. The apparatus for electrochemical measurements according to claim 5, wherein the through-hole has a cross sectional area of 1 $\mu m^2$ or greater and 2,500 $\mu m^2$ or less.

8. The apparatus for electrochemical measurements according to claim 5, wherein the lower layer has a thickness of 5 $\mu m$ or greater and 100 $\mu m$ or less.

9. The apparatus for electrochemical measurements according to claim 5, wherein the surface area of the auxiliary electrode is no less than 10 times greater than the assembly of the oxidation electrodes.

10. The apparatus for electrochemical measurements according to claim 5, wherein a mesh filter is provided on an upper of the upper layer.

11. The apparatus for electrochemical measurements according to claim 5, wherein the reference electrode is formed on an upper face of the upper layer, while the auxiliary electrode is formed on a lower face of the lower layer.

12. A process for quantitatively determining a target substance included in a sample solution, with an apparatus for electrochemical measurements comprising a reference electrode, an auxiliary electrode and an electrode plate for electrochemical measurements, or a counter electrode and an electrode plate for electrochemical measurements, the process comprising the steps of:

preparing a sample solution containing an electronic mediator;

providing the electrode plate for electrochemical measurements;

bringing the reference electrode, the auxiliary electrode and the electrode plate for electrochemical measurements into contact with the sample solution, or bringing the counter electrode and the electrode plate for electrochemical measurements into contact with the sample solution;

measuring the electric current that flows each of the oxidation electrode plate and the reduction electrode, by sweeping a positive potential to the oxidation electrode plate and applying a negative potential to the reduction electrode plate, or by applying a positive potential to the oxidation electrode plate and sweeping a negative potential to the reduction electrode plate; and determining the amount of the target substance from the electric current derived in the step of measuring the electric current, wherein said electrode plate for electrochemical measurements comprising a substrate made of an insulator, an upper layer made of insulator provided on an upper face of the substrate, and a lower layer made of an insulator provided on a lower face of the substrate, wherein:

the substrate comprises a plurality of oxidation electrodes sandwiched between the upper face of the substrate and the upper layer, and a plurality of reduction electrodes sandwiched between the lower face of the substrate and the lower layer;

the upper layer comprises a plurality of upper layer openings;

each of the oxidation electrodes is exposed from each of the upper layer openings;

the lower layer comprises a plurality of lower layer openings;

each of the reduction electrodes is exposed from each of the lower layer openings;

the substrate is provided with a plurality of through-holes that penetrate from the upper face of each of the oxidation electrodes to the lower face of each of the reduction electrodes;

each of the upper layer openings has the same area with an area of each of the lower layer openings;

each of the upper layer openings has an area of equal to or less than 10,000 $\mu m^2$, and each of the lower layer openings has an area of equal to or less than 10,000 $\mu m^2$.

13. The process according to claim 12, wherein each of the upper layer openings has an area of equal to or greater than 225 $\mu m^2$, and each of the lower layer openings has an area of equal to or greater than 225 $\mu m^2$.

14. The process according to claim 12, wherein the through-hole has a cross sectional area of 1 $\mu m^2$ or greater and 2,500 $\mu m^2$ or less.

15. The process according to claim 12, wherein the lower layer has a thickness of 5 μm or greater and 100 μm or less.

16. The process according to claim 12, wherein the surface area of the auxiliary electrode is no less than 10 times greater than the assembly of the oxidation electrodes.

17. The process according to claim 12, wherein a mesh filter is provided on an upper face of the upper layer.

18. The process according to claim 12, wherein the reference electrode is formed on an upper face of the upper layer, while the auxiliary electrode is formed on a lower face of the lower layer.

* * * * *